United States Patent
Pate et al.

(10) Patent No.: US 11,285,028 B2
(45) Date of Patent: Mar. 29, 2022

(54) VASCULAR STENT DEVICES AND METHODS

(71) Applicant: TVA Medical, Inc., Franklin Lakes, NJ (US)

(72) Inventors: Thomas D. Pate, Austin, TX (US); William E. Cohn, Bellaire, TX (US)

(73) Assignee: TVA MEDICAL, INC., Franklin Lakes, NJ (US)

( * ) Notice: Subject to any disclaimer, the term of this patent is extended or adjusted under 35 U.S.C. 154(b) by 318 days.

(21) Appl. No.: 16/335,157

(22) PCT Filed: Jul. 19, 2017

(86) PCT No.: PCT/US2017/042937
§ 371 (c)(1),
(2) Date: Mar. 20, 2019

(87) PCT Pub. No.: WO2018/057095
PCT Pub. Date: Mar. 29, 2018

(65) Prior Publication Data
US 2019/0274855 A1    Sep. 12, 2019

Related U.S. Application Data

(60) Provisional application No. 62/399,465, filed on Sep. 25, 2016.

(51) Int. Cl.
*A61F 2/95* (2013.01)
*A61B 18/14* (2006.01)
(Continued)

(52) U.S. Cl.
CPC ............... *A61F 2/95* (2013.01); *A61B 17/11* (2013.01); *A61B 18/1492* (2013.01); *A61F 2/82* (2013.01);
(Continued)

(58) Field of Classification Search
CPC .... A61F 2/07; A61F 2/064; A61F 2/95; A61F 2/82; A61F 2250/001; A61F 2250/0039;
(Continued)

(56) References Cited

U.S. PATENT DOCUMENTS

| 3,649,850 A | 3/1972 | Davis |
| 3,827,436 A | 8/1974 | Stumpf et al. |

(Continued)

FOREIGN PATENT DOCUMENTS

| CA | 2883209 A1 | 4/2014 |
| CN | 1730123 A | 2/2006 |

(Continued)

OTHER PUBLICATIONS

Extended European Search Report pertaining to EP Patent Application No. 17853586.0, dated Apr. 29, 2020.
(Continued)

*Primary Examiner* — Tan-Uyen T Ho
*Assistant Examiner* — Chima U Igboko
(74) *Attorney, Agent, or Firm* — Dinsmore & Shohl LLP

(57) ABSTRACT

Described here are devices, systems, and methods for cannulating a vessel. Generally, the method may comprise advancing a stent into a first vessel and deploying the stent in the first vessel to hold open one or more valves. This may permit retrograde blood flow through the blood vessel in peripheral vasculature and aid in cannulation of the blood vessel.

13 Claims, 15 Drawing Sheets

(51) Int. Cl.
  *A61M 1/36* (2006.01)
  *A61F 2/90* (2013.01)
  *A61F 2/82* (2013.01)
  *A61B 17/11* (2006.01)
  *A61B 18/00* (2006.01)
  *A61B 17/00* (2006.01)
  *A61B 90/00* (2016.01)

(52) U.S. Cl.
  CPC ............ *A61F 2/90* (2013.01); *A61M 1/3655* (2013.01); *A61B 2017/00022* (2013.01); *A61B 2017/00057* (2013.01); *A61B 2017/00115* (2013.01); *A61B 2017/00876* (2013.01); *A61B 2017/1107* (2013.01); *A61B 2017/1139* (2013.01); *A61B 2018/00214* (2013.01); *A61B 2018/00404* (2013.01); *A61B 2018/00577* (2013.01); *A61B 2018/00601* (2013.01); *A61B 2090/376* (2016.02); *A61B 2090/3966* (2016.02); *A61F 2250/0036* (2013.01); *A61M 1/3661* (2014.02); *A61M 2205/0288* (2013.01)

(58) Field of Classification Search
  CPC ............... A61F 2/90; A61F 2250/0036; A61B 17/3468; A61B 2017/00252; A61B 2090/3966; A61B 2090/376; A61B 2018/00577; A61B 17/11; A61B 18/1492; A61B 2017/00876; A61B 2017/1139; A61B 2017/00115; A61B 2017/00057; A61B 2017/00022; A61B 2017/1107; A61B 2018/00601; A61B 2018/00214; A61B 2018/00404; A61M 1/3655; A61M 2205/0288; A61M 1/3661
  See application file for complete search history.

(56) References Cited

U.S. PATENT DOCUMENTS

| | | |
|---|---|---|
| 4,416,664 A | 11/1983 | Womack |
| 4,802,475 A | 2/1989 | Weshahy |
| 5,313,943 A | 5/1994 | Houser et al. |
| 5,697,909 A | 12/1997 | Eggers et al. |
| 5,800,487 A | 9/1998 | Mikus et al. |
| 5,830,222 A | 11/1998 | Makower |
| 5,830,224 A | 11/1998 | Cohn et al. |
| 5,895,404 A | 4/1999 | Ruiz |
| 5,971,979 A | 10/1999 | Joye et al. |
| 6,004,330 A | 12/1999 | Middleman et al. |
| 6,032,677 A | 3/2000 | Blechman et al. |
| 6,039,730 A | 3/2000 | Rabin et al. |
| 6,068,638 A | 5/2000 | Makower |
| 6,099,542 A | 8/2000 | Cohn et al. |
| 6,159,225 A | 12/2000 | Makower |
| 6,190,353 B1 | 2/2001 | Makower et al. |
| 6,197,025 B1 | 3/2001 | Grossi et al. |
| 6,217,575 B1 | 4/2001 | DeVore et al. |
| 6,231,587 B1 | 5/2001 | Makower |
| 6,256,525 B1 | 7/2001 | Yang et al. |
| 6,283,988 B1 | 9/2001 | Laufer et al. |
| 6,287,306 B1 | 9/2001 | Kroll et al. |
| 6,302,875 B1 * | 10/2001 | Makower ............ A61B 8/12 604/528 |
| 6,327,505 B1 | 12/2001 | Medhkour et al. |
| 6,347,247 B1 | 2/2002 | Dev et al. |
| 6,355,029 B1 | 3/2002 | Joye et al. |
| 6,357,447 B1 | 3/2002 | Swanson et al. |
| 6,379,353 B1 | 4/2002 | Nichols |
| 6,383,180 B1 | 5/2002 | Lalonde et al. |
| 6,400,976 B1 | 6/2002 | Champeau |
| 6,428,534 B1 | 8/2002 | Joye et al. |
| 6,461,356 B1 | 10/2002 | Patterson |
| 6,464,665 B1 | 10/2002 | Heuser |
| 6,464,723 B1 | 10/2002 | Callol |
| 6,468,268 B1 | 10/2002 | Abboud et al. |
| 6,475,214 B1 | 11/2002 | Moaddeb |
| 6,475,226 B1 | 11/2002 | Belef et al. |
| 6,527,724 B1 | 3/2003 | Fenici |
| 6,527,769 B2 | 3/2003 | Langberg et al. |
| 6,542,766 B2 | 4/2003 | Hall et al. |
| 6,544,230 B1 | 4/2003 | Flaherty et al. |
| 6,569,158 B1 | 5/2003 | Abboud et al. |
| 6,569,162 B2 | 5/2003 | He |
| 6,579,311 B1 | 6/2003 | Makower |
| 6,585,650 B1 | 7/2003 | Solem |
| 6,592,577 B2 | 7/2003 | Abboud et al. |
| 6,635,053 B1 | 10/2003 | Lalonde et al. |
| 6,655,386 B1 | 12/2003 | Makower et al. |
| 6,656,173 B1 | 12/2003 | Palermo |
| 6,663,625 B1 | 12/2003 | Ormsby et al. |
| 6,669,709 B1 | 12/2003 | Cohn et al. |
| 6,673,085 B1 | 1/2004 | Berg |
| 6,676,657 B2 | 1/2004 | Wood |
| 6,682,525 B2 | 1/2004 | Lalonde et al. |
| 6,695,878 B2 | 2/2004 | McGuckin et al. |
| 6,709,444 B1 | 3/2004 | Makower |
| 6,719,756 B1 | 4/2004 | Muntermann |
| 6,726,697 B2 | 4/2004 | Nicholas et al. |
| 6,733,494 B2 | 5/2004 | Abboud et al. |
| 6,736,808 B1 | 5/2004 | Motamedi et al. |
| 6,761,708 B1 | 7/2004 | Chiu et al. |
| 6,761,714 B2 | 7/2004 | Abboud et al. |
| 6,780,181 B2 | 8/2004 | Kroll et al. |
| 6,849,073 B2 | 2/2005 | Hoey et al. |
| 6,855,143 B2 | 2/2005 | Davison et al. |
| 6,887,234 B2 | 5/2005 | Abboud et al. |
| 6,911,026 B1 | 6/2005 | Hall et al. |
| 6,932,814 B2 | 8/2005 | Wood |
| 6,936,024 B1 | 8/2005 | Houser |
| 6,960,209 B2 | 11/2005 | Clague et al. |
| 6,971,983 B1 | 12/2005 | Cancio |
| 6,981,972 B1 | 1/2006 | Farley et al. |
| 7,059,330 B1 | 6/2006 | Makower et al. |
| 7,060,063 B2 | 6/2006 | Marion et al. |
| 7,094,235 B2 | 8/2006 | Francischelli |
| 7,155,293 B2 | 12/2006 | Westlund et al. |
| 7,179,270 B2 | 2/2007 | Makower |
| 7,189,231 B2 | 3/2007 | Clague et al. |
| 7,214,234 B2 | 5/2007 | Rapacki et al. |
| 7,231,260 B2 | 6/2007 | Wallace et al. |
| 7,250,051 B2 | 7/2007 | Francischelli |
| 7,288,075 B2 | 10/2007 | Parihar et al. |
| 7,303,554 B2 | 12/2007 | Lalonde et al. |
| 7,306,598 B2 | 12/2007 | Truckai et al. |
| 7,335,198 B2 | 2/2008 | Eggers et al. |
| 7,341,063 B2 | 3/2008 | Garbibaldi et al. |
| 7,367,341 B2 | 5/2008 | Anderson et al. |
| 7,374,567 B2 | 5/2008 | Heuser |
| 7,387,636 B2 | 6/2008 | Cohn et al. |
| 7,407,506 B2 | 8/2008 | Makower |
| 7,628,768 B2 | 12/2009 | Faul et al. |
| 7,702,387 B2 | 4/2010 | Stevenson et al. |
| 7,727,268 B2 | 6/2010 | Cunniffe et al. |
| 7,744,596 B2 | 6/2010 | Young et al. |
| 7,811,281 B1 | 10/2010 | Rentrop |
| 7,828,814 B2 | 11/2010 | Brenneman et al. |
| 7,846,172 B2 | 12/2010 | Makower |
| 7,849,860 B2 | 12/2010 | Makower et al. |
| 7,857,809 B2 | 12/2010 | Drysen |
| 7,881,797 B2 | 2/2011 | Griffin et al. |
| 7,955,326 B2 | 6/2011 | Paul et al. |
| 7,967,769 B2 | 6/2011 | Faul et al. |
| 7,967,770 B2 | 6/2011 | Li et al. |
| 8,010,208 B2 | 8/2011 | Nimer et al. |
| 8,048,016 B2 | 11/2011 | Faul et al. |
| 8,052,680 B2 | 11/2011 | Hassett et al. |
| 8,062,321 B2 | 11/2011 | Heuser et al. |
| RE43,007 E | 12/2011 | Lalonde et al. |
| 8,075,555 B2 | 12/2011 | Truckai et al. |
| 8,088,171 B2 | 1/2012 | Brenneman |
| 8,100,899 B2 | 1/2012 | Doty et al. |
| 8,118,809 B2 | 2/2012 | Paul et al. |
| 8,135,467 B2 | 3/2012 | Markowitz et al. |

(56) References Cited

U.S. PATENT DOCUMENTS

| | | |
|---|---|---|
| 8,142,454 B2 | 3/2012 | Harrison et al. |
| 8,192,425 B2 | 6/2012 | Mirza et al. |
| 8,200,466 B2 | 6/2012 | Spilker et al. |
| 8,226,592 B2 | 7/2012 | Brenneman et al. |
| 8,231,618 B2 | 7/2012 | Viswanathan et al. |
| 8,236,014 B2 | 8/2012 | Brenneman et al. |
| 8,262,649 B2 | 9/2012 | Francischelli |
| 8,273,095 B2 | 9/2012 | Brenneman et al. |
| 8,328,797 B2 | 12/2012 | Wilson et al. |
| 8,333,758 B2 | 12/2012 | Joye et al. |
| 8,361,061 B2 | 1/2013 | Esch et al. |
| 8,366,707 B2 | 2/2013 | Kassab et al. |
| 8,382,697 B2 | 2/2013 | Brenneman et al. |
| 8,409,196 B2 | 4/2013 | Durgin et al. |
| 8,413,664 B2 | 4/2013 | Appling |
| 8,414,572 B2 | 4/2013 | Davison et al. |
| 8,419,681 B2 | 4/2013 | Sell |
| 8,439,909 B2 | 5/2013 | Wang et al. |
| 8,454,587 B2 | 6/2013 | Lalonde et al. |
| 8,475,441 B2 | 7/2013 | Babkin et al. |
| 8,486,062 B2 | 7/2013 | Belhe et al. |
| 8,486,064 B2 | 7/2013 | Van Wyk et al. |
| 8,551,032 B2 | 10/2013 | Faul et al. |
| 8,574,185 B2 | 11/2013 | Faul et al. |
| 8,585,700 B2 | 11/2013 | Katou |
| 8,608,754 B2 | 12/2013 | Wensel et al. |
| 8,641,724 B2 | 2/2014 | Brenneman et al. |
| 8,649,879 B2 | 2/2014 | DiGiore et al. |
| 8,676,309 B2 | 3/2014 | Deem et al. |
| 8,685,014 B2 | 4/2014 | Babkin et al. |
| 8,700,179 B2 | 4/2014 | Pianca et al. |
| 8,715,281 B2 | 5/2014 | Barlow et al. |
| 8,758,334 B2 | 6/2014 | Coe et al. |
| 8,771,267 B2 | 7/2014 | Kunis et al. |
| 8,784,409 B2 | 7/2014 | Robilotto et al. |
| 8,790,341 B2 | 7/2014 | Pappone et al. |
| 8,876,699 B2 | 11/2014 | Sato et al. |
| 8,876,815 B2 | 11/2014 | Coe et al. |
| 8,882,765 B2 | 11/2014 | Kassab et al. |
| 8,911,435 B2 | 12/2014 | Katoh et al. |
| 8,951,251 B2 | 2/2015 | Willard |
| 9,017,323 B2 | 4/2015 | Miller et al. |
| 9,039,702 B2 | 5/2015 | Miller et al. |
| 9,072,880 B2 | 7/2015 | Phillips et al. |
| 9,089,316 B2 | 7/2015 | Baust et al. |
| 9,108,018 B2 | 8/2015 | Dickinson et al. |
| 9,155,827 B2 | 10/2015 | Franano |
| 9,204,916 B2 | 12/2015 | Lalonde |
| 9,259,340 B2 | 2/2016 | Heuser et al. |
| 9,283,034 B2 | 3/2016 | Katoh et al. |
| 9,307,992 B2 | 4/2016 | Wilson et al. |
| 9,314,329 B2 | 4/2016 | Dickinson et al. |
| 9,326,792 B2 | 5/2016 | Dickinson et al. |
| 9,364,280 B2 | 6/2016 | Zarins et al. |
| 9,402,560 B2 | 8/2016 | Organ et al. |
| 9,414,885 B2 | 8/2016 | Willard |
| 9,439,728 B2 | 9/2016 | Hull et al. |
| 9,445,868 B2 | 9/2016 | Hull et al. |
| 9,452,015 B2 | 9/2016 | Kellerman et al. |
| 9,486,276 B2 | 11/2016 | Rios et al. |
| 9,623,217 B2 | 4/2017 | Pillai |
| 9,706,998 B2 | 7/2017 | Dickinson et al. |
| 9,782,201 B2 | 10/2017 | Dickinson et al. |
| 9,782,533 B2 | 10/2017 | Brenneman et al. |
| 10,045,817 B2 | 8/2018 | Miller et al. |
| 10,265,206 B2 | 4/2019 | Heuser et al. |
| 10,517,637 B2 | 12/2019 | Dickinson et al. |
| 10,543,308 B2 | 1/2020 | Lenihan et al. |
| 10,575,974 B2 | 3/2020 | De Pablo Pena et al. |
| 10,596,356 B2 | 3/2020 | Lenihan et al. |
| 2001/0029384 A1 | 10/2001 | Nicholas et al. |
| 2002/0072739 A1 | 6/2002 | Lee et al. |
| 2002/0113678 A1 | 8/2002 | Creighton |
| 2002/0151945 A1 | 10/2002 | Gobin et al. |
| 2003/0009163 A1 | 1/2003 | Messing et al. |
| 2003/0220674 A1 | 11/2003 | Anderson et al. |
| 2004/0059211 A1 | 3/2004 | Patel et al. |
| 2004/0059280 A1 | 3/2004 | Makower et al. |
| 2004/0098095 A1 | 5/2004 | Burnside et al. |
| 2004/0167506 A1 | 8/2004 | Chen |
| 2004/0215220 A1 | 10/2004 | Dolan et al. |
| 2004/0236360 A1 | 11/2004 | Cohn et al. |
| 2005/0033401 A1 | 2/2005 | Cunniffe et al. |
| 2005/0065509 A1 | 3/2005 | Coldwell et al. |
| 2005/0245925 A1 | 11/2005 | Iki et al. |
| 2005/0251120 A1 | 11/2005 | Anderson et al. |
| 2006/0079897 A1 | 4/2006 | Harrison et al. |
| 2006/0111704 A1 | 5/2006 | Brenneman et al. |
| 2007/0173878 A1 | 7/2007 | Heuser |
| 2007/0185567 A1 | 8/2007 | Heuser et al. |
| 2007/0203515 A1 | 8/2007 | Heuser et al. |
| 2007/0203572 A1 | 8/2007 | Heuser et al. |
| 2007/0293856 A1 | 12/2007 | Paul et al. |
| 2008/0021532 A1 | 1/2008 | Kveen et al. |
| 2008/0051626 A1 | 2/2008 | Sato et al. |
| 2008/0065019 A1 | 3/2008 | Heuser et al. |
| 2008/0091192 A1 | 4/2008 | Paul et al. |
| 2008/0119879 A1 | 5/2008 | Brenneman et al. |
| 2008/0140061 A1 | 6/2008 | Toubia et al. |
| 2008/0161901 A1 | 7/2008 | Heuser et al. |
| 2008/0171944 A1* | 7/2008 | Brenneman ............ A61B 17/11 600/509 |
| 2008/0183164 A1 | 7/2008 | Elkins et al. |
| 2008/0188848 A1 | 8/2008 | Deutmeyer et al. |
| 2008/0275442 A1 | 11/2008 | Paul et al. |
| 2008/0312577 A1 | 12/2008 | Drasler et al. |
| 2009/0036872 A1 | 2/2009 | Fitzgerald et al. |
| 2009/0076324 A1 | 3/2009 | Takayama et al. |
| 2009/0093791 A1 | 4/2009 | Heuser |
| 2009/0112119 A1 | 4/2009 | Kim |
| 2009/0118722 A1 | 5/2009 | Ebbers et al. |
| 2009/0124847 A1 | 5/2009 | Doty et al. |
| 2009/0157014 A1* | 6/2009 | Osborne ............ A61M 39/0208 604/264 |
| 2009/0198232 A1 | 8/2009 | Young et al. |
| 2009/0248148 A1 | 10/2009 | Shaolian et al. |
| 2009/0275876 A1 | 11/2009 | Brenneman et al. |
| 2009/0281379 A1 | 11/2009 | Binmoeller et al. |
| 2009/0318849 A1 | 12/2009 | Hobbs et al. |
| 2010/0004623 A1 | 1/2010 | Hamilton, Jr. et al. |
| 2010/0010488 A1 | 1/2010 | Kassab et al. |
| 2010/0082058 A1 | 4/2010 | Kassab |
| 2010/0130835 A1 | 5/2010 | Brenneman et al. |
| 2010/0198206 A1 | 8/2010 | Levin |
| 2010/0204691 A1 | 8/2010 | Bencini |
| 2010/0222664 A1 | 9/2010 | Lemon et al. |
| 2010/0256616 A1 | 10/2010 | Katoh et al. |
| 2010/0280316 A1 | 11/2010 | Dietz et al. |
| 2010/0280514 A1 | 11/2010 | Zerfas et al. |
| 2010/0286705 A1 | 11/2010 | Vassiliades, Jr. |
| 2010/0292685 A1 | 11/2010 | Katoh et al. |
| 2010/0298645 A1 | 11/2010 | Deutch |
| 2010/0318180 A1* | 12/2010 | Porter ...................... A61F 2/91 623/1.16 |
| 2011/0015657 A1 | 1/2011 | Brenneman et al. |
| 2011/0112427 A1 | 5/2011 | Phillips et al. |
| 2011/0118735 A1 | 5/2011 | Abou-Marie et al. |
| 2011/0201990 A1 | 8/2011 | Franano |
| 2011/0213309 A1 | 9/2011 | Young et al. |
| 2011/0218476 A1 | 9/2011 | Kraemer et al. |
| 2011/0270149 A1 | 11/2011 | Faul et al. |
| 2011/0288392 A1 | 11/2011 | de la Rama et al. |
| 2011/0288544 A1 | 11/2011 | Verin et al. |
| 2011/0306959 A1 | 12/2011 | Kellerman et al. |
| 2011/0306993 A1 | 12/2011 | Hull et al. |
| 2011/0319976 A1 | 12/2011 | Iyer et al. |
| 2012/0010556 A1 | 1/2012 | Faul et al. |
| 2012/0022518 A1 | 1/2012 | Levinson |
| 2012/0035539 A1 | 2/2012 | Tegg |
| 2012/0046678 A1 | 2/2012 | LeMaitre et al. |
| 2012/0059398 A1 | 3/2012 | Pate et al. |
| 2012/0065652 A1 | 3/2012 | Cully et al. |
| 2012/0078342 A1 | 3/2012 | Vollkron et al. |
| 2012/0089123 A1 | 4/2012 | Organ et al. |

(56) References Cited

U.S. PATENT DOCUMENTS

| | | |
|---|---|---|
| 2012/0101423 A1 | 4/2012 | Brenneman |
| 2012/0116354 A1 | 5/2012 | Heuser |
| 2012/0157992 A1 | 6/2012 | Smith et al. |
| 2012/0209377 A1 | 8/2012 | Machold et al. |
| 2012/0215088 A1 | 8/2012 | Wang et al. |
| 2012/0239021 A1 | 9/2012 | Doty et al. |
| 2012/0277736 A1 | 11/2012 | Francischelli |
| 2012/0281330 A1 | 11/2012 | Abbott et al. |
| 2012/0289953 A1 | 11/2012 | Berzak et al. |
| 2012/0296262 A1 | 11/2012 | Ogata et al. |
| 2012/0302935 A1* | 11/2012 | Miller ............... A61B 18/1492 604/8 |
| 2013/0041306 A1 | 2/2013 | Faul et al. |
| 2013/0056876 A1 | 3/2013 | Harvey et al. |
| 2013/0110105 A1 | 5/2013 | Vankov |
| 2013/0172881 A1 | 7/2013 | Hill et al. |
| 2013/0190744 A1 | 7/2013 | Avram et al. |
| 2013/0190754 A1 | 7/2013 | Paul et al. |
| 2013/0216351 A1 | 8/2013 | Griffin |
| 2013/0226170 A1 | 8/2013 | Seddon et al. |
| 2013/0261368 A1 | 10/2013 | Schwartz |
| 2013/0282000 A1 | 10/2013 | Parsonage |
| 2014/0031674 A1 | 1/2014 | Newman et al. |
| 2014/0094791 A1 | 4/2014 | Hull et al. |
| 2014/0100557 A1 | 4/2014 | Bohner et al. |
| 2014/0100562 A1 | 4/2014 | Sutermeister et al. |
| 2014/0107642 A1* | 4/2014 | Rios ............... A61B 18/1492 606/41 |
| 2014/0166098 A1 | 6/2014 | Kian et al. |
| 2014/0188028 A1 | 7/2014 | Brenneman et al. |
| 2014/0276335 A1 | 9/2014 | Pate |
| 2015/0005759 A1 | 1/2015 | Welches et al. |
| 2015/0011909 A1 | 1/2015 | Holmin et al. |
| 2015/0018810 A1 | 1/2015 | Baust et al. |
| 2015/0057654 A1 | 2/2015 | Leung et al. |
| 2015/0057687 A1 | 2/2015 | Gittard et al. |
| 2015/0080886 A1 | 3/2015 | Miller et al. |
| 2015/0094645 A1 | 4/2015 | Omar-Pasha |
| 2015/0112195 A1 | 4/2015 | Berger et al. |
| 2015/0126965 A1* | 5/2015 | Liungman ............ A61M 25/04 604/509 |
| 2015/0134055 A1 | 5/2015 | Spence et al. |
| 2015/0141836 A1 | 5/2015 | Naumann et al. |
| 2015/0164573 A1 | 6/2015 | Delaney |
| 2015/0196356 A1 | 7/2015 | Kauphusman et al. |
| 2015/0196360 A1 | 7/2015 | Grantham et al. |
| 2015/0201962 A1 | 7/2015 | Kellerman et al. |
| 2015/0258308 A1 | 9/2015 | Pate |
| 2015/0297259 A1 | 10/2015 | Matsubara et al. |
| 2015/0313668 A1 | 11/2015 | Miller et al. |
| 2015/0320472 A1 | 11/2015 | Ghaffari et al. |
| 2016/0022345 A1 | 1/2016 | Baust et al. |
| 2016/0058452 A1 | 3/2016 | Brenneman et al. |
| 2016/0058956 A1 | 3/2016 | Cohn et al. |
| 2016/0067449 A1 | 3/2016 | Misener et al. |
| 2016/0082234 A1 | 3/2016 | Schwartz et al. |
| 2016/0128855 A1 | 5/2016 | Heuser et al. |
| 2016/0135881 A1 | 5/2016 | Katoh et al. |
| 2016/0184011 A1 | 6/2016 | Krishnan |
| 2016/0206317 A1* | 7/2016 | Dickinson ............ A61F 2/958 |
| 2017/0119464 A1 | 5/2017 | Rios et al. |
| 2017/0172679 A1 | 6/2017 | Doty et al. |
| 2017/0202603 A1 | 7/2017 | Cohn et al. |
| 2017/0202616 A1 | 7/2017 | Pate et al. |
| 2018/0000512 A1 | 1/2018 | Dickinson et al. |
| 2018/0083228 A1 | 3/2018 | Yang et al. |
| 2018/0116522 A1 | 5/2018 | Brenneman et al. |
| 2018/0206845 A1 | 7/2018 | Brenneman et al. |
| 2018/0344396 A1 | 12/2018 | Miller et al. |
| 2020/0061338 A1 | 2/2020 | Pate |

FOREIGN PATENT DOCUMENTS

| | | |
|---|---|---|
| CN | 101730557 A | 6/2010 |
| EP | 0923912 A2 | 6/1999 |
| JP | 3127126 | 11/2006 |
| RU | 2168951 C1 | 6/2001 |
| WO | 9956640 A1 | 11/1999 |
| WO | 2006105008 A1 | 10/2006 |
| WO | 2008010039 A2 | 1/2008 |
| WO | 2009005644 A2 | 1/2009 |
| WO | 2011100625 A2 | 8/2011 |
| WO | 2013112584 A1 | 8/2013 |
| WO | 2014052919 A1 | 4/2014 |
| WO | 2015061614 A1 | 4/2015 |
| WO | 2015085119 A1 | 6/2015 |
| WO | 2015108984 A1 | 7/2015 |
| WO | 2016033380 A1 | 3/2016 |
| WO | 2017124059 A1 | 7/2017 |
| WO | 2017124060 A1 | 7/2017 |
| WO | 2018057095 A1 | 3/2018 |

OTHER PUBLICATIONS

Extended European Search Report for EP Application No. 17739123. 2.

Maybury et al., "The Effect of Roll Angle on the Performance of Halbach Arrays," University of California—San Diego, Center for Magnetic Recording Research (2008), 19 pgs.

Choi, et al., Design of a Halbach Magnet Array Based on Optimization Techniques; IEEE Transactions on Magnetics, vol. 44, No. 10, Oct. 2008, pp. 2361-2366. (Year: 2008).

"Banasik et al. (2011).""A rare variant route of the ulnar artery does not contraindicate the creation of a fistula in the wrist of a diabetic patient with end-stage renal disease,""Postepy Hig Med Dosw. 65:654-657."

Bharat et al. (2012) "A novel technique of vascular anastomosis to prevent juxta-anastomotic stenosis following arteriovenous fistula creation," J. Vascular Surgery 55(1):274-280.

Bode et al. (2011 ). "Clinical study protocol for the arch project Computational modeling for improvement of outcome after vascular access creation," J. Vasc. Access 12(4):369-376.

Hakim et al., "Ulnar artery-based free forearm flap: Review of Specific anatomic features in 322 cases and related literature," Heand & Neck, Dec. 2013 (published online:2014), Wiley Online Library.

Davidson, I. et al. (2008). "Duplex Ultrasound Evaluation for Dialysis Access Selection and Maintenance: A Practical Guide," The Journal of Vascular Access 9(1 ): 1-9.

Gracz, et al. (1977). "Proximal forearm fistula for maintenance hemodialysis," Kidney International 11 :71-75.

Jennings, WC. et al. (2011). "Primary arteriovenous fistula inflow proximalization for patients at high risk for dialysis access-associated ischemic steal syndrome," J Vasc. Surgery 54(2):554-558.

Kinnaert, et al. (1971). "Ulnar Arteriovenous Fistula for Maintenance Haemodial Ysis," British J. Surgery 58(9):641-643.

Morale et al. (2011). "Venae comitantes as a potential vascular resource to create native arteriovenous fistulae," J. Vasc. Access 12(3):211-214.

Shenoy, S. (2009). "Surgical anatomy of upper arm: what is needed for AVF planning," The Journal of Vascular Access 10:223-232.

Vachharajani, T. (2010). "Atlas of Dialysis Vascular Access," Wake Forest University School of Medicine, 77 total pages.

Whittaker et al. (2011). "Prevention better than cure. Avoiding steal syndrome with proximal radial or ulnar arteriovenous fistulae" J. Vasc. Access 12(4):318-320.

Office Action dated Jun. 4, 2021, pertaining to Japanese Patent Application No. 2019-516190.

Office Action pertaining to corresponding Japanese Patent Application No. 2018-536423, dated Feb. 12, 2021.

\* cited by examiner

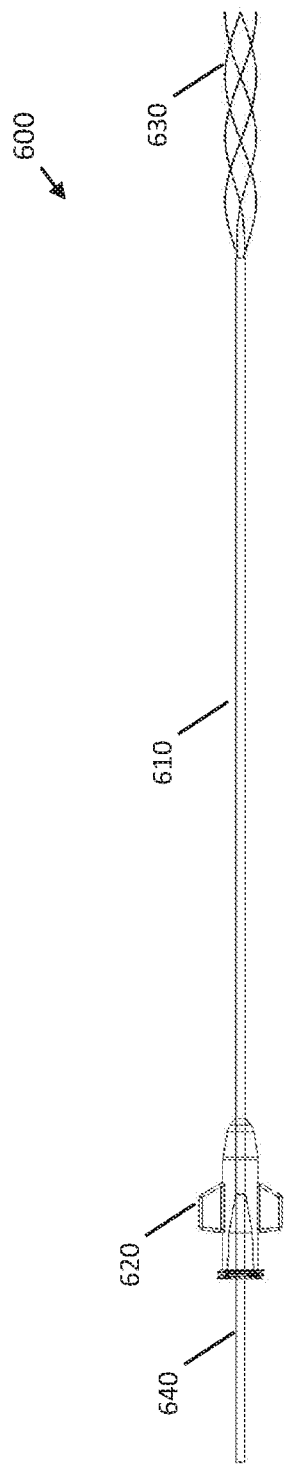

VASCULAR STENT DEVICES AND METHODS

CROSS-REFERENCE TO RELATED APPLICATIONS

This application claims priority to U.S. Provisional Application Ser. No. 62/399,465, filed on Sep. 25, 2016, and titled "VASCULAR STENT DEVICES AND METHODS," the content of which is incorporated by reference in its entirety.

FIELD

The current invention relates to stents and methods for cannulating a vessel.

BACKGROUND

An intravenous cannula provides access to a vein and may allow blood to be drawn and fluids to be administered into a patient. In the case of hemodialysis, cannulation provides access to a fistula with quickened blood flow that may provide for effective dialysis. In dialysis treatment, needles, catheters, or other cannulas may be inserted into the blood vessels near a fistula to draw blood from the circulatory system, pass it through a dialysis machine, and return it to the body. However, cannulation can be difficult due to challenges in locating vessel sites, difficulty reaching vessels for vascular access due to an underlying layer of adipose tissue, collapse of a blood vessel being punctured, and complications from cannulation that may include hematoma, infiltration, thrombosis, and embolism. It would therefore be useful to find improved ways to access the vasculature for cannulation, and ways to modify blood flow to allow for alternative access sites, such as to improve access to blood vessels near a fistula.

BRIEF SUMMARY

Described here are devices, systems, and methods for improving retrograde blood flow through peripheral vasculature and to aid in cannulation. The devices, systems, and methods described herein may be used to hold open venous valves to allow bi-directional flow of blood through a vein. In some variations, a stent may be deployed in a blood vessel to hold open a valve to increase retrograde blood flow, aid in locating the blood vessel, and structurally support the blood vessel during cannulation. In some variations, a fistula may be formed to arterialize a vein and increase retrograde blood flow through the vein. In some variations, the methods described herein comprise methods for cannulating a first vessel comprising advancing a stent into the first vessel comprising one or more valves. The stent may be deployed over one or more valves to hold open the one or more valves. A needle may be advanced through a wall of the first vessel. In some variations, the needle may also be advanced through an aperture defined in a wall of the stent. In other variations, the needle may be advanced through the wall of the first vessel at a location distal to the stent. In some variations, stent location may be detected non-invasively. In some of these variations, the needle may be positioned over the first vessel using the detected stent location. In other variations, the stent comprises first struts and second struts having different thicknesses. In some variations, the first vessel may be a cephalic vein. In other variations, the first vessel may be a basilic vein.

In some variations, a first catheter may be advanced into an artery adjacent to a vein. The first catheter may comprise a fistula-forming element, and a fistula may be formed between the artery and the vein using the fistula-forming element. The stent may be deployed distal to the fistula. The artery may be an ulnar artery and the vein may be an ulnar vein. A second catheter may be advanced into the vein. In some instances, the first catheter and the second catheter may be aligned. One or more stents may be loaded into a third catheter. The one or more stents may be sequentially deployed from the third catheter into the first vessel by advancing a push wire through the third catheter.

Also described here are systems for forming a fistula and improving retrograde blood flow through peripheral vasculature. In general, the systems described herein may include a catheter system comprising a stent comprising one or more apertures defined in a wall of the stent. The stent may be configured to hold open one or more venous valves and receive a needle through one or more apertures. A first catheter may comprise a fistula-forming element. In some variations, the stent may comprise first struts and second struts having different thicknesses. The system may further comprise a plurality of the stents and a second catheter comprising a push wire configured to deploy one or more stents sequentially from a distal end of the second catheter. The fistula-forming element may be an electrode. The needle may be a cannula. The system may further comprise a stent detector coupled to a needle injector coupled to the needle.

BRIEF DESCRIPTION OF THE DRAWINGS

FIG. 6 depicts an illustrative variation of a stent delivery system.

DETAILED DESCRIPTION

Generally described here are devices, systems, and methods for providing a stent in peripheral vasculature to permit retrograde blood flow, to support cannulation of a vein, and/or to percutaneously create one or more arteriovenous fistulae for increasing venous blood flow, such as for increasing retrograde blood flow through a forearm vein to be cannulated. Accordingly, it may be helpful to briefly describe the anatomy of the vasculature of the arm.

Figure 1:
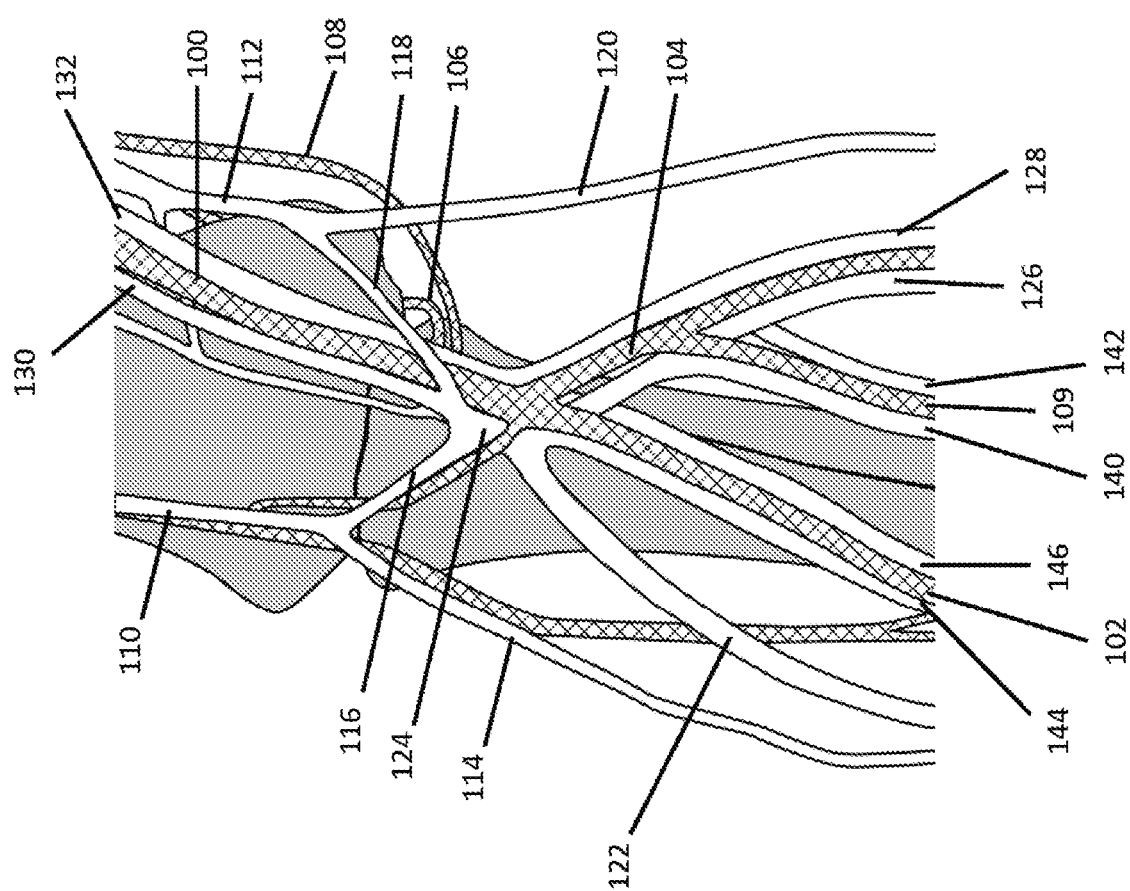
FIG. 1 is an illustrative depiction of the vascular anatomy of the arm.

FIG. 1 shows a simplified depiction of the typical vascular anatomy of the arm around the elbow. Specifically, FIG. 1 shows an anterior view of the right arm as would be seen with the palm facing upward. As shown there, the brachial artery (100) extends superficially and distally from the upper arm and sinks deeply into the arm near the elbow joint, where the brachial artery (100) branches into the radial artery (102) and the ulnar artery (104). The upper portion of the ulnar artery (104) is deeply seated within the arm beneath the superficial flexor muscles (not shown), and leads down the ulnar side of the forearm to the wrist. The anterior ulnar recurrent artery (106) and the posterior ulnar recurrent artery (108) branch off of the ulnar artery (104) just below the elbow joint, and these arteries supply blood to the joint and surrounding muscles. Further down the arm (typically just below the radial tuberosity of the radius bone (not shown)), the interosseous artery (109) branches off from the ulnar artery (104) and eventually feeds into the posterior and anterior interosseous arteries.

Also shown in FIG. 1 are the cephalic vein and the basilic vein. The cephalic vein runs along the outer border of the bicep muscle (not shown) continues down into the forearm (the cephalic vein of the upper arm is labeled in FIG. 1 as cephalic vein (110), while the cephalic vein of the lower arm is labeled as cephalic vein (114)). The median cephalic vein (116) joins the cephalic vein2 (110, 114) near the elbow joint. The basilic vein runs along the inner side of the bicep muscle and continues into the forearm (the basilic vein of the upper arm is labeled as basilic vein (112), while the basilic vein of the lower arm is labeled as common ulnar vein (120)). The basilic vein (120) of the lower arm is sometimes referred to as the common ulnar vein. The median cubital vein (118) (in some instances referred to as the median basilic vein) joins the basilic vein (112) and the common ulnar vein (120) (in some instances, this vein segment is also referred to as the basilic vein of the forearm). The median cubital vein (118) and the median cephalic vein (116) are formed at the branching of the median antebrachial vein (122). Near the branching of the median vein (122) into the median cubital vein (118) and the medial cephalic vein (116), a perforating branch (124) connects these vessels with the deep veins of the arm through the antebrachial fascia (not shown). As shown in FIG. 1, perforating branch (124) communicates with a first deep ulnar vein (126) and a second deep ulnar vein (128). These deep ulnar veins (126, 128) may run substantially parallel on either side of the ulnar artery (104) between the brachial artery (100) and the interosseous artery (109), and may branch away from ulnar artery (104) distal to the interosseous artery (109). Between the brachial artery (100) and the interosseous artery (109), the deep ulnar veins are typically located in close proximity to the ulnar artery, and usually less than 2 mm separate the ulnar artery from the deep ulnar veins. Along the length of the deep ulnar veins, transverse branches (not shown) may occasionally connect the deep ulnar veins. Also shown in FIG. 1 are first brachial vein (130) and second (132) brachial vein. The brachial veins generally run along the brachial artery (100), and the deep ulnar veins feed into the brachial veins near the elbow joint. Additionally, a pair of radial veins (not shown) may run along the radial artery, and may feed into one or both of the brachial veins.

Generally, the systems, devices, and methods described herein may be used to hold open venous valves to permit retrograde blood flow in a blood vessel, to assist in locating a vascular access site, and/or to provide structural support to a blood vessel to aid in cannulation (e.g., needle puncture into the blood vessel). In some variations, one or more of these uses may be in conjunction with formation of a fistula between two blood vessels (e.g., an arteriovenous fistula between an artery and a vein). In some variations, a delivery system may be utilized to deploy one or more structures (e.g., stents) in a target blood vessel where the deployed structures may increase blood flow and aid in cannulation.

Generally, the systems and methods may be used to hold open unidirectional venous valves in a vein to allow arterialized blood flow (e.g., from an arteriovenous fistula between an artery and a vein) to travel distally through the vein and provide a preferred conduit for retrograde blood flow. Generally, to create a retrograde blood flow path through a vein, a stent may be advanced in a minimally invasive manner through the vasculature to a peripheral vein (e.g., a vein segment in the forearm). The stent may be placed in the peripheral vein to hold open one or more venous valves to permit retrograde blood flow. For example, the sidewalls of the stent may push one or more unidirectional valves against the inner circumference of the vein so as to hold open the valves in the vein without damaging them. Opening the valves using a stent may allow blood to flow retrograde through the vein without removing the venous valves, as would be required in a valvulotomy procedure. For example, opening the valves using a stent may allow arterialized blood flow from a fistula to flow retrograde through the vein without removing the venous valves. As the venous valves in the rest of the peripheral vasculature retain their function and inhibit retrograde flow, the portion of the vein having the stent provides a preferred retrograde blood flow pathway. The devices and systems described herein offer a reversible approach to rendering valves incompetent having improved procedural speed relative to a valvulotome that cuts the leaflets of the valves. In some instances, a single stent may be placed in a blood vessel. In other instances, a system comprising multiple stents may be deployed in one or more blood vessels. For example, in some instances, a stent may be placed in each of two veins (e.g., a cephalic vein and a basilic vein). In other instances, a stent may be placed in a vein and an accessory vein. It should be appreciated that each stent may or may not have the same configuration of elements, and that some stents may be different from and/or complementary to other stents.

Also generally described are systems comprising one or more stents to aid in cannulating a blood vessel by reducing damage and/or preventing collapse of the blood vessel being punctured. The stent may add radial strength and stiffness to the blood vessel in which it is disposed. These stents may be the same or different stents as those allowing retrograde venous blood flow. The one or more stents generally comprise a plurality of struts and may vary in length, diameter, thickness, geometric patterns, compressibility, and flexibility based on a target vessel, function, and delivery process. The stent may comprise a cannulation region having one or more apertures defined in a wall of the stent configured to receive a needle such as for cannulation.

Generally, the devices, systems and methods described herein may be used to cannulate a vein, such as a forearm vein. Generally, a stent may be advanced in a minimally invasive manner through the vasculature and placed in the vein. The stent may add to the strength and stiffness of the vein segment in which the stent is disposed, such as when being punctured by a needle. In some instances, the vein may be palpated and/or visualized to locate one or more of the stent and vein for cannulation. In other instances, the system may comprise a stent detector to non-invasively detect the stent disposed in the vein. For example, the stent detector may generate a signal when the presence of the stent is detected through the skin of the patient and output the signal to an operator. In some of these instances, a stent may define a cannulation region through which a needle may be advanced. Once a vein is located, an insertion point may be selected for a cannula such as a needle. The needle may be advanced through the skin and a vessel wall of the vein and an aperture defined in a wall (e.g., sidewall) of the stent. By advancing the needle through the vessel wall and stent having enhanced strength and stiffness, complications from cannulation such as infiltration, hematoma, and vein wall collapse may be reduced.

Generally, the systems described herein may comprise a stent detector and cannulator. These devices and systems may detect and locate the blood vessel for cannulation in cases where visualization and palpation are insufficient. In some variations, the stent detector may comprise a metal detector configured to detect a metal stent disposed in a vein. In some variations, the stent detector may comprise an output device to indicate to an operator the detected location of the stent under the skin. The cannulator (e.g., needle injector) may be coupled to a needle that may be advanced through skin and into a wall of a blood vessel and an aperture defined in a wall of the stent. In some instances, the system may output an audio tone when the system is located over the stent in the blood vessel.

Generally, one or more stents may be advanced in a minimally invasive manner through the vasculature and placed in the vein using a stent delivery system. These devices and systems offer a minimally invasive approach that may improve procedural speed by permitting deployment of one or more stents using a single catheter and deployment to smaller diameter blood vessels. Generally, to deliver and deploy one or more stents, one or more catheters may be advanced in a minimally invasive fashion through the vasculature to a target location. In some instances, a single catheter may be advanced to a target site in a blood vessel to deploy one or more stents. In other instances, a system comprising multiple catheters may be used to deliver and deploy one or more stents to target sites in respective blood vessels. For example, in some instances a catheter may be placed in each of the two blood vessels (e.g., different veins). One or both of the catheters may comprise a push wire (e.g., guidewire, stylet, push rod). The push wire may be configured to slide within the catheter to advance one or more stents out of a lumen of the catheter for deployment of a stent. For example, one or more stents may be loaded into a lumen of the catheter distal to the push wire. The stent may be configured to self-deploy to a predetermined shape when advanced out of the catheter and into a target blood vessel by the push wire. For example, a distal tip of the push wire may push a proximal end of the stent through a catheter lumen and out the distal end of the catheter. In these instances, it should be appreciated that each catheter may or may not have the same configuration of elements, and that some catheters may be different from and/or complementary to other catheters.

Generally, the systems and methods may be used to form and access a fistula in peripheral vasculature, such as in a forearm. These devices and systems offer a minimally invasive approach that may improve procedural speed. Generally, to form one or more fistulas between two blood vessels, one or more catheters may be advanced in a minimally invasive fashion through the vasculature to a target location. In some instances, a single catheter may be placed in a blood vessel to form a fistula with an adjoining blood vessel. In other instances, a system comprising multiple catheters may be used to form one or more fistulas. For example, in some instances a catheter may be placed in each of the two blood vessels (e.g., an artery and a vein). One or both of the catheters may comprise a fistula-forming element. The fistula-forming element(s) may comprise an electrode that is used to form the fistula such as through tissue ablation. The catheter may further comprise one or more alignment portions including magnets that help align one catheter relative to another catheter in related blood vessels and/or bring the catheters (and blood vessels) in closer approximation. In these instances, it should be appreciated that each catheter may or may not have the same configuration of elements, and that some catheters may be different from and/or complementary to other catheters.

I. Systems

The systems described here may comprise one or more stents to hold open one or more valves of a venous blood vessel, provide structural support to a vein in which it is disposed, and/or aid in access for cannulation. Generally, the stents may comprise a plurality of struts forming a cylindrical configuration. The stent may be placed in a blood vessel to hold the valves in an open configuration that allows bi-directional blood flow, and in particular, retrograde blood flow through a vein. Accordingly, it may be desirable that the stent have sufficient radial strength to hold open the valves, but be of minimal thickness and surface area (e.g., diaphanous) to limit platelet activation and stenosis. The radial strength, thickness, and surface area of the stents described herein may be significantly less than that of vascular stents for maintaining the patency of blood vessels. In some variations, a stent may hold one or more valves open, allow at least one of blood flow from a fistula and a needle to pass through an aperture defined in a sidewall of the stent, and provide structural support to the fistula.

A. Stent

Figure 2A:
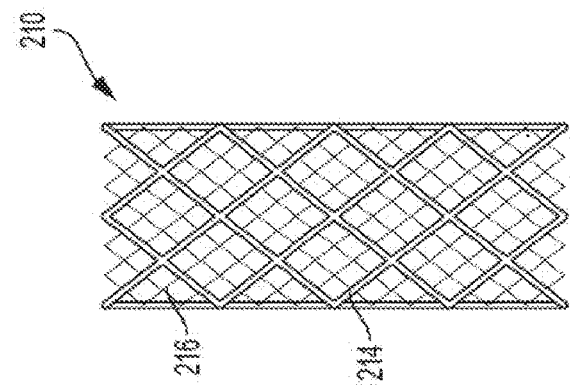
FIGS. 2A-2F depict illustrative variations of a stent.

FIGS. 2A-2F show illustrative variations of stent geometries that may be used to increase retrograde blood flow in venous vasculature. FIG. 2A shows a portion of a stent (200). As shown there, the stent (200) may comprise a plurality of struts (204) forming a repeating symmetric diamond pattern, which forms a cylindrical configuration (202). It should be understood that many different configurations of the stent pattern may be used to provide a structure capable of holding the valve leaflets open. Patterns may include a helical coil or coils, rings of straight, angled, zig-zag, or curved geometries interconnected by linking elements, or braided or woven meshes.

Figure 2B:
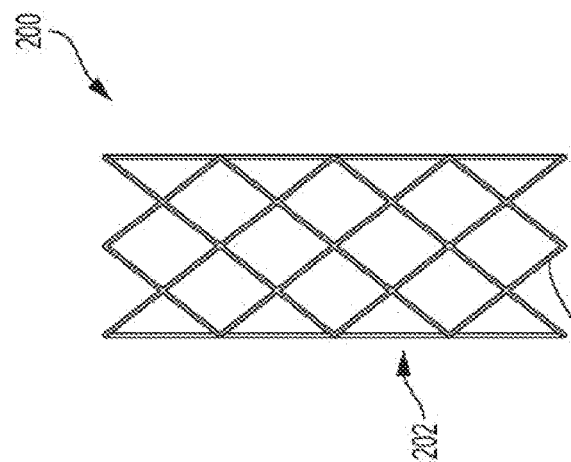
Figure 2C:
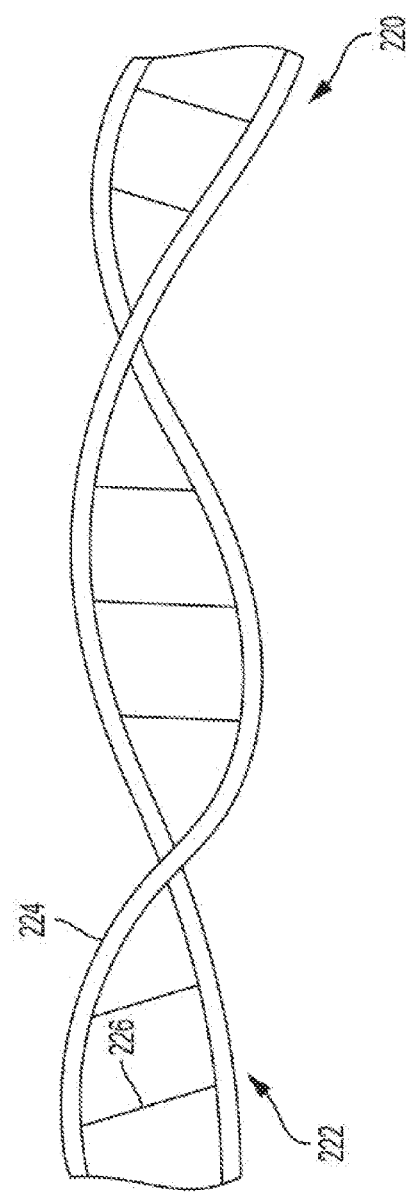

Another variation is illustrated in FIG. 2B, which shows a portion of a stent (210) comprising a plurality of first struts (214) and a plurality of second struts (216) forming a cylindrical configuration (212). The first struts (214) may be thicker (e.g., have a larger diameter) than the second struts (216). In one example, the first struts (214) may form a first set of diamonds and the second struts (216) may form a second set of diamonds within the larger diamonds. As shown, nine smaller diamonds form a larger diamond. In some variations, the second struts (216) may be disposed on the interior side of the first struts (214). The first struts (214) may be configured to provide radial strength to a blood vessel in which the stent (210) is disposed. The second struts (216) may be configured to hold open the valves. In some variations, one or more of the larger diamonds formed by the first struts (214) may be formed without second struts (216) such that the larger diamond defines an aperture (not shown). The first and second struts (214, 216) thus form the sidewalls of the stent. An example of struts defining an aperture is further described herein. In yet another variation, as shown in FIG. 2C, a stent (220) may comprise a helical configuration. For example, the stent (220) may comprise a double helix (222) comprising two or a plurality of helical elongate struts (224) and a plurality of connecting struts (226).

Figure 2D:
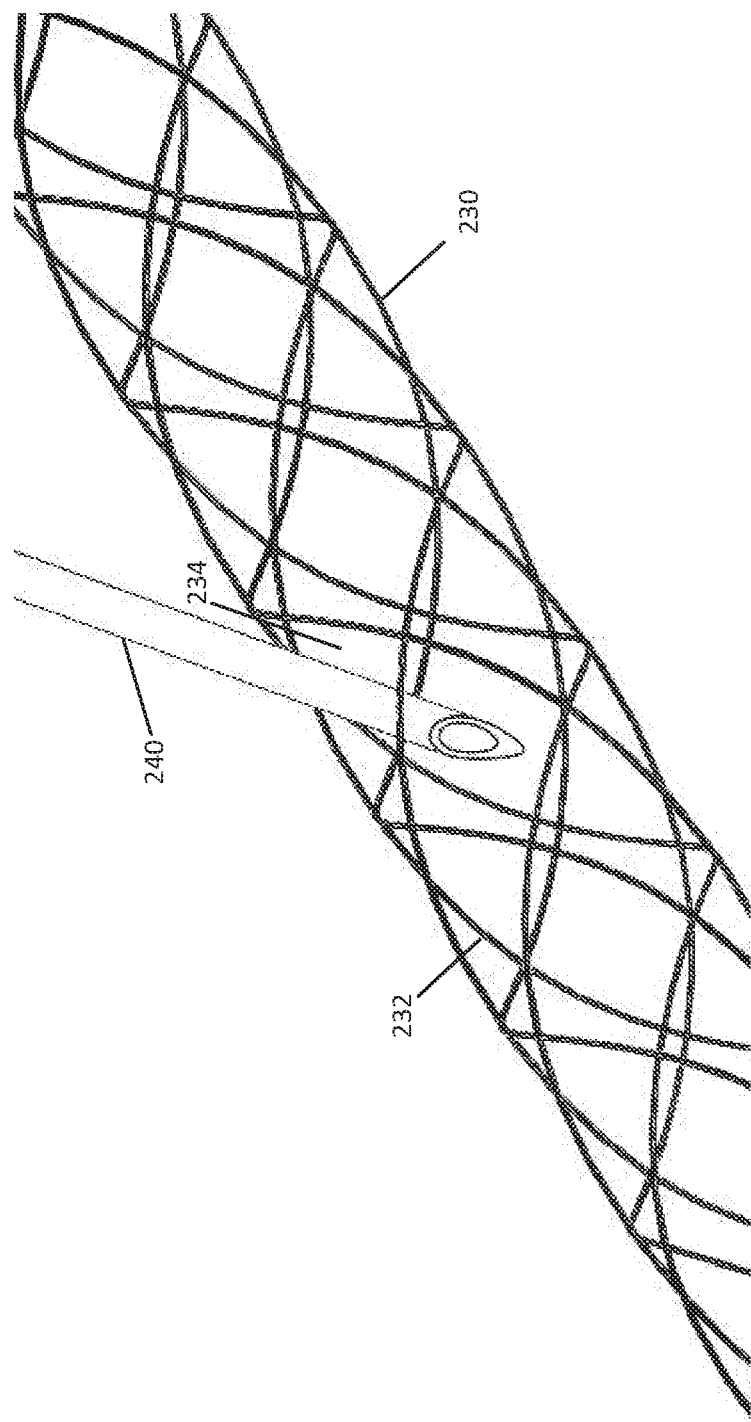
Figure 2E:
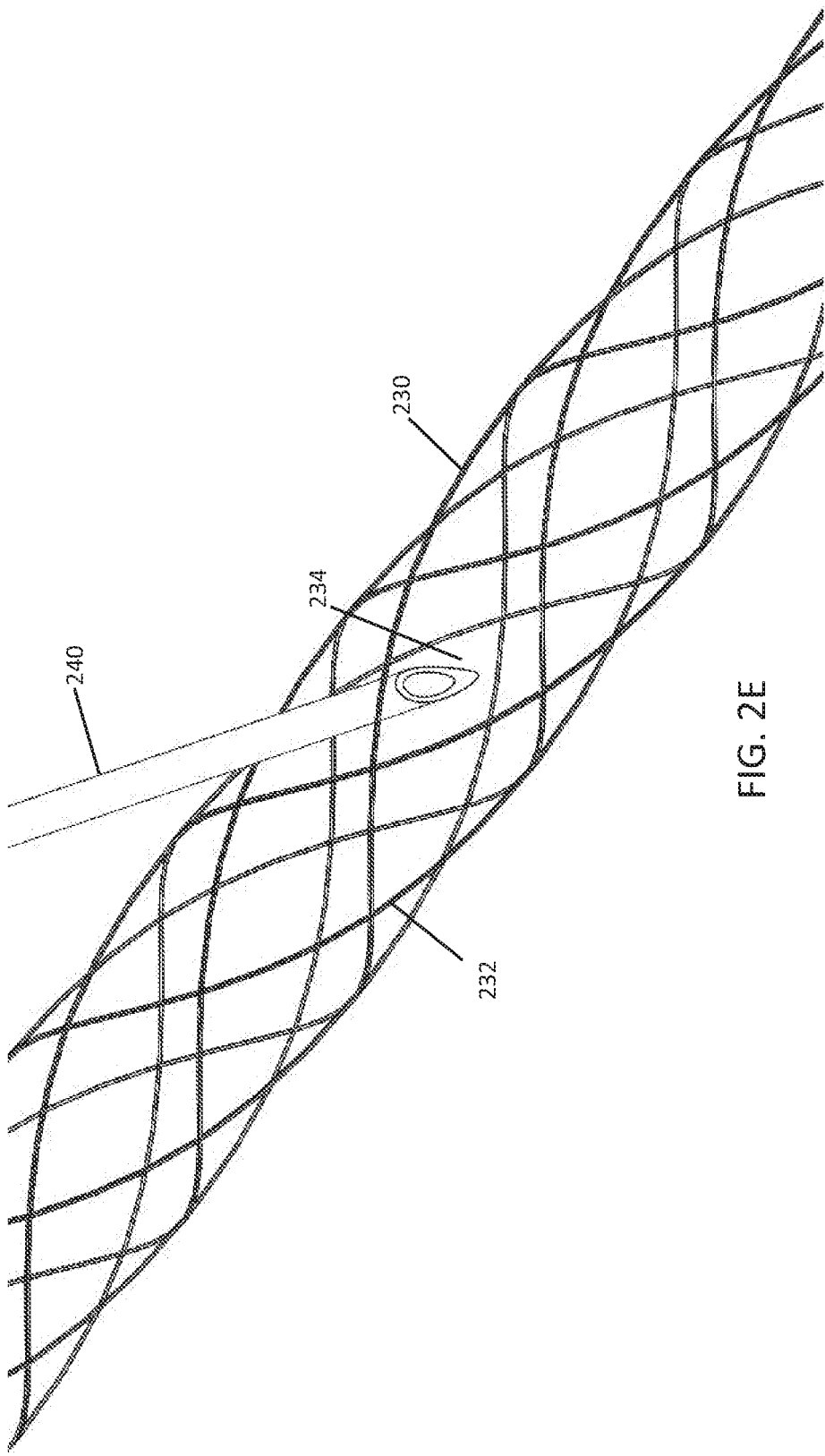
Figure 2F:
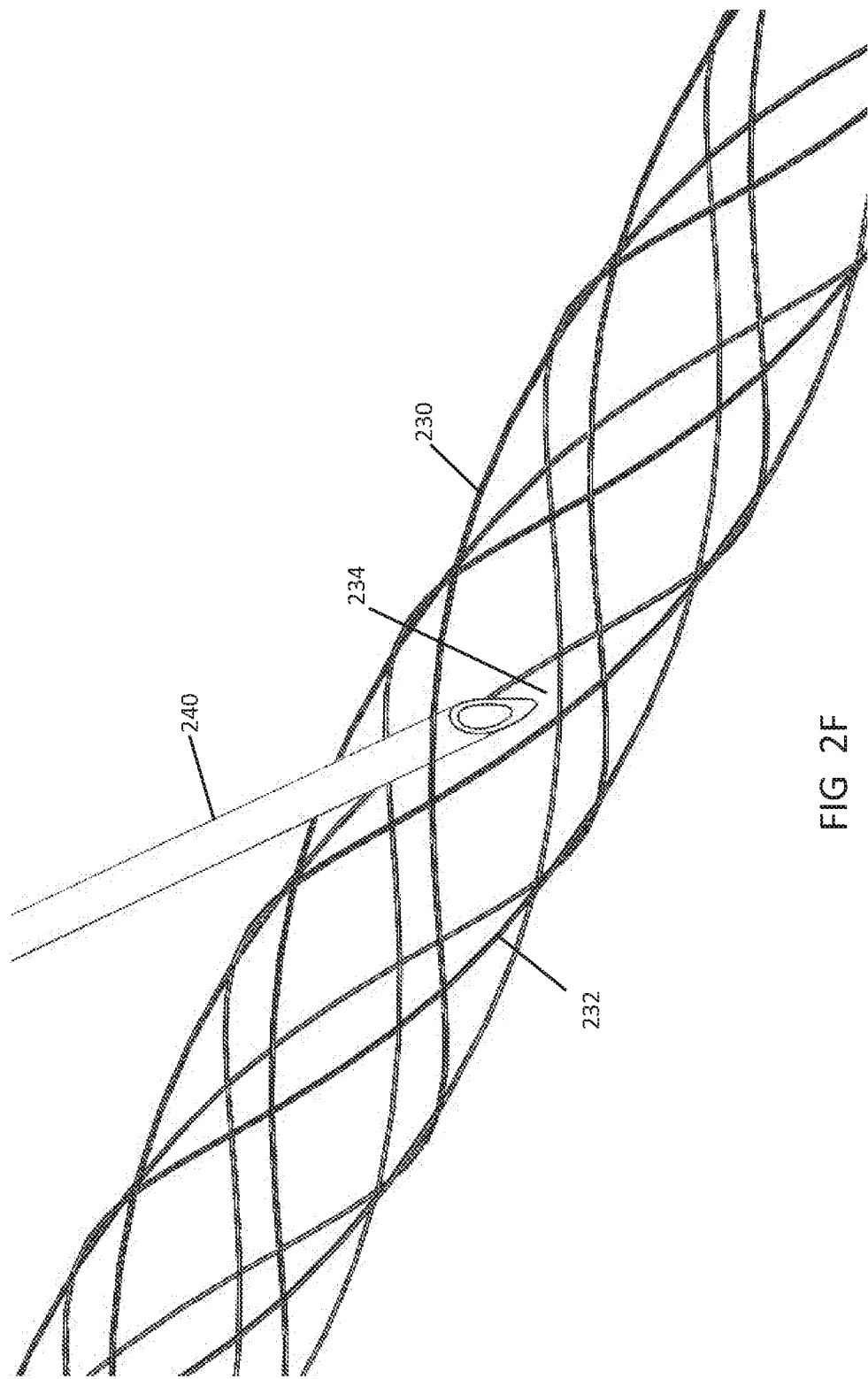

FIGS. 2D-2F illustrates a portion of a stent (230) comprising a plurality of struts (232) arranged to form one or more apertures (234) defined in a wall of the strut and disposed along a length of the strut and configured to receive a needle (240). For example, the struts (232) may form a quadrilateral aperture (234). In some variations, the aperture (234) may be configured to receive a needle (240) having a diameter between about 12 gauge and about 20 gauge. In some variations, the struts (232) forming the aperture may add radial stiffness to locally support a wall of the vein being punctured by the needle (240) to allow the vein to be punctured without collapsing. A needle advanced through a wall of a target blood vessel may be further advanced through an aperture (234) of the stent (230) without contact and/or damage to a strut (232). As such, the stent (230) may form a cannulation region along its length through which a needle (240) may preferably be advanced.

In some variations, the stents may be configured with dimensions to hold open venous valves and/or support the vessel during cannulation. In some variations, the stent may have an outer diameter between about 1 mm and about 20 mm. For example, the stent may have an outer diameter of about 5.0 mm. In some variations, the stent may have a strut width and thickness between about 0.05 mm and about 0.5 mm. In some variations, the stent may have side aperture openings disposed in a plane parallel to a longitudinal axis of the strut (e.g., the apertures being substantially orthogonal to the longitudinal axis of the strut) having a length between about 1 mm and about 15 mm and a width between about 1 mm and about 15 mm. For example, the stent may have an outer diameter of about 5.0 mm, a strut width of about 0.05 mm, a strut thickness of about 0.05 mm, and one or more diamond shaped apertures about 5 mm in width and about 10 mm in length.

In some variations, an axial portion of the stent may comprise a plurality of struts. For example, an axial portion of the stent may comprise a minimum of four struts to provide a predetermined minimum strut-to-leaflet ratio to achieve adequate valve leaflet opening when deployed in a vein. In some instances, the strut width and mesh density of the stent may be minimized so as to achieve a minimum stent area-to-intimal area ratio. In some variations, the strut surface area-to-vessel wall surface area ratio may be between about 0.02 and about 0.08. In some instances, this ratio may be between about 0.03 and about 0.04. The stent may comprise any suitable configuration, such as a cylindrical configuration (e.g., tube) and/or helical spiral configuration. In some variations, the stent may have a length between about 5.0 cm and about 60 cm. For example, the stent may have a length of about 15.0 cm. The stent may be configured to fit within a lumen of a target blood vessel and press against the leaflets of a valve, such that they are moved into and held in an open configuration until the stent is removed.

The stent may be made of any suitable material, for example, one or more metals or polymers (e.g., stainless steel 316L, tantalum, nitinol, platinum iridium, niobium alloy, cobalt alloy, etc.). The stent may optionally be bioresorbable (e.g., made of poly-L lactic acid (PLLA) and may absorb over a time period of six months to three years) and may optionally comprise a drug eluting coating configured to prevent stenosis and/or thrombosis). The stent may be formed by any suitable manufacturing process, for example, laser cutting, photochemical etching, braiding, knitting, vapor deposition, water jet, etc. In some variations, the stent may comprise one or more coverings and/or visualization markers to aid in locating and positioning the stent within a vessel. For example, the stent may comprise a radiopaque marker and/or coating made of one or more of gold, platinum, tantalum, etc. that may be indirectly visualized.

In some variations, the stent may comprise multiple portions, each portion corresponding to a specific material, shape, and/or coating. For example, the stent may comprise a proximal portion comprising a coating for inducing thrombosis, a distal portion configured to prevent platelet aggregation and maximize fluid flow through the vessel, and an intermediate portion comprising a radiopaque marker surrounding an aperture and configured to permit visualization to aid in locating a blood vessel for cannulation. Of course, the stent may comprise any suitable number of portions (e.g., two, three, or four portions) and the length of each portion may be the same or different from the other portions. The stent may comprise any suitable length, and the length of the stent may vary depending on the type of procedure being performed.

In some variations, one or more portions of the stent may comprise a visual detection portion for indirectly visualizing the location and/or orientation of a stent with respect to a catheter system, target blood vessel, and/or external elements such as a cannulator. The visual detection portion may be visualized using a technique such as fluoroscopy during stent deployment and/or needle puncture of the blood vessel. In some instances, one or more characteristics of the stent such as echogenicity, radiopacity, surface area, surface area, permittivity, conductivity, permeability, and the like may be selected to enhance detection by, for example, fluoroscopy and/or a stent detector described herein. Fluoroscopy is a technique for real-time X-ray imaging where, generally, an X-ray beam is emitted from a fluoroscope through an area of interest in a body. Objects to be visualized (e.g., stents) may be imaged using an image intensifier. A user viewing the real-time images shown by the image intensifier may then determine the location and orientation of the one or more stents and use it to guide stent deployment and/or needle insertion.

Generally, a visual detection portion may be configured such that an aperture defined in a wall of the stent is discernable in a two-dimensional fluoroscopic image and/or detectable by a stent detector. In some variations, the portions of the stent configured for non-invasive detection may be used to guide positioning of a needle to be inserted through an aperture of the stent and the vessel wall. For example, one or more detection portions of the stent may surround an aperture of the stent and/or be provided at a predetermined location corresponding to the aperture. In some instances, the detection portions of the stent may comprise a set of patterns that may be visualized under fluoroscopy. For example, the visual detection portion may comprise an ellipsoid or polygon that may be fluoroscopically imaged. The shape of the visual detection portion may vary on a fluoroscopic image based on an orientation of the stent relative to the image intensifier. For example, a circular visual detection portion surrounding an aperture of the stent that appears as an ellipsoid on a fluoroscopic image may indicate that the aperture is non-perpendicular with respect to the image intensifier. Accordingly, the visual detection portion may be used to guide placement of a stent in a target blood vessel and/or cannula insertion through an aperture of the stent.

B. Stent Detector

Figure 3:
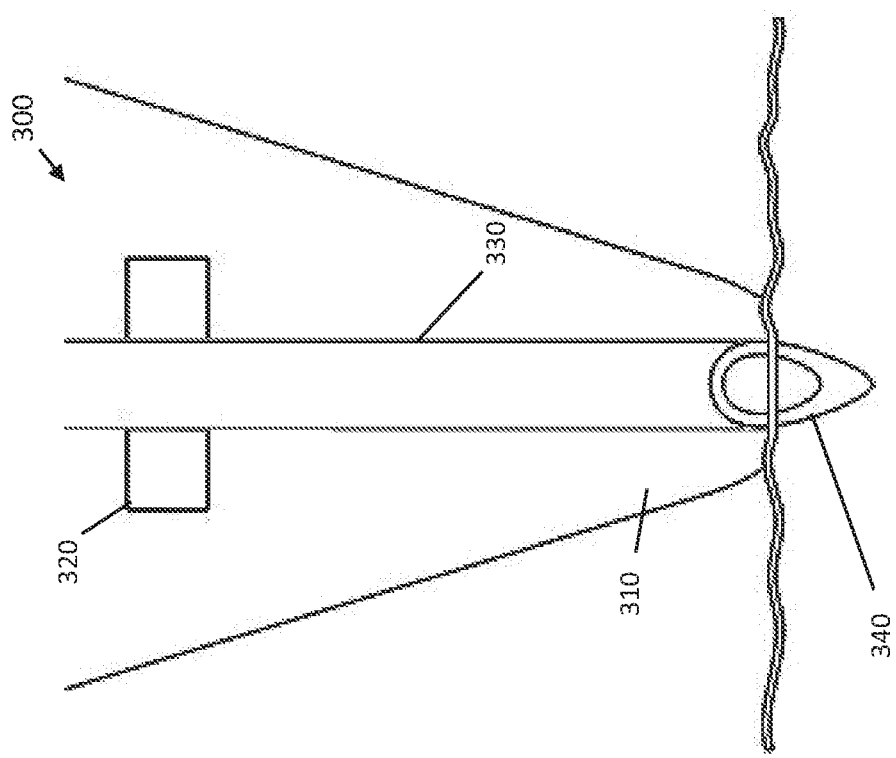
FIG. 3 depicts an illustrative variation of a system described here comprising a stent detector and cannulator.

The systems described here may comprise one or more of a stent detector configured to locate a stent disposed in a vessel and a cannulator (e.g., needle injector) configured to advance a needle through a wall of the blood vessel and the stent. FIG. 3 illustrates a side view of a cannulation system (300). As shown in FIG. 3, a stent detector (300) may comprise a sensor (310) configured to detect a stent, an output device (320) configured to output a stent detection status, a cannulator (330), and a needle (340). The sensor (310) may be configured to non-invasively detect a location of a stent disposed in a blood vessel to aid an operator in positioning the cannulator (330) and the needle (340) for cannulation. In some variations, the sensor (310) may comprise a metal detector configured to generate a stent signal in response to detecting a metal content of a stent disposed in a blood vessel. In some instances, the sensor (310) may comprise an inductive sensor. In some variations, the stent detector (300) may comprise an optical source configured to project a light into the skin and an optical sensor configured to receive the reflected light from the skin that is used to generate the stent signal.

The output device (320) may receive the stent signal and use it to generate a signal to indicate that the stent has been located within a predetermined volume of space (e.g., the stent is directly beneath the location of the stent detector (300)). The output device (320) may output one or more signals to indicate a location of the stent relative to the stent detector (300). For example, the output device (320) may generate one or more audible tones and/or beeps to indicate proximity to a stent. In some variations, a set of colored lights may be output by the output device (320) to visually indicate a distance between the stent detector (300) and the stent. In some instances, the color, pattern, intensity, and number of lights may correspond to different ranges of distances between the stent detector (300) and the stent.

The output device (320) may comprise one or more of a display device, audio device, and haptic device. In some variations, the display device may be configured to display a graphical user interface (GUI). A display device may permit an operator to view patient data, sensor data, system data, alarms, and/or warnings. In some variations, an output device may comprise a display device including at least one of a light emitting diode (LED), liquid crystal display (LCD), electroluminescent display (ELD), plasma display panel (PDP), thin film transistor (TFT), organic light emitting diodes (OLED), and the like. An audio device may audibly output patient data, sensor data, system data, alarms, and/or warnings. For example, the audio device may output an audible warning when an operator actuates the stent detector (300) to inject the needle (340) when a stent is not detected within a predetermined range by the stent detector (300). In some variations, an audio device may comprise at least one of a speaker, piezoelectric audio device, magnetostrictive speaker, and/or digital speaker. A haptic device may provide additional sensory output (e.g., force feedback) to the operator. For example, a haptic device may generate a tactile response (e.g., vibration) to provide an alarm and/or warning. For example, haptic feedback may notify that operation of the cannulator is inhibited to prevent potential harm to the patient when a stent is not detected within a predetermined range. In some variations, the stent detector (300) may comprise a wired and/or wireless transmitter configured to transmit a stent signal to another device such as an external computing device including a desktop computer, server, database, and the like.

In some variations, a needle (340) may be advanced through the skin when the stent detector (300) locates the stent. The cannulator (330) may comprise a lumen to guide the needle (340). The needle (340) may be may be manually advanced from the cannulator (330) and/or actuated by the cannulator (330). The lumen may be configured to hold a needle (340) of any suitable size for cannulation, such as between about 12 gauge and about 20 gauge. The cannulator (330) may be configured to actuate when the stent is detected within a predetermined range to ensure that a needle (340) will advance through an aperture of the stent. Operation of the cannulator (330) may be inhibited and a notification output when the operator attempts to actuate the cannulator (330) when the stent is detected outside a predetermined range.

The stent detector (300) may comprise one or more processors and one or more machine-readable memories in communication with the one or more processors. The processor may incorporate data received from memory, sensor data, and operator input to control the stent detector (300). For example, the processor and memory may receive the stent signal from the sensor and determine a distance of the sensor to a stent. In some instance, the processor may compare the stent signal to a look-up-table. The processor may then select one or more notification methods based on the determined distance and user settings. The memory may further store instructions to cause the processor to execute modules, processes and/or functions associated with the stent detector (300). The processor and memory may be implemented consistent with numerous general purpose or special purpose computing systems or configurations. Various exemplary computing systems, environments, and/or configurations that may be suitable for use with the systems and devices disclosed herein may include, but are not limited to software or other components within or embodied on computing devices such as routing/connectivity components, multiprocessor systems, microprocessor-based systems, distributed computing networks, personal computing devices, network appliances, portable (e.g., hand-held) or laptop devices.

The processor may be any suitable processing device configured to run and/or execute a set of instructions or code and may include one or more data processors, image processors, graphics processing units, physics processing units, digital signal processors, and/or central processing units. The processor may be, for example, a general purpose processor, Field Programmable Gate Array (FPGA), an Application Specific Integrated Circuit (ASIC), and/or the like. The processor may be configured to run and/or execute application processes and/or other modules, processes and/or functions associated with the system and/or a network associated therewith. The underlying device technologies may be provided in a variety of component types such as metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

In some variations, the memory may include a database and may be, for example, a random access memory (RAM), a memory buffer, a hard drive, an erasable programmable read-only memory (EPROM), an electrically erasable read-only memory (EEPROM), a read-only memory (ROM), Flash memory, and the like. As used herein, database refers to a data storage resource. The memory may store instructions to cause the processor to execute modules, processes and/or functions associated with the control system, such as stent detection, notification, calibration, cannulation, and/or device settings. In some variations, storage may be network-based and accessible for one or more authorized users. Network-based storage may be referred to as remote data storage or cloud data storage. Some variations described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs); Compact Disc-Read Only Memories (CD-ROMs); holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other variations described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

C. Stent Delivery System

Generally, one or more stents may be advanced in a minimally invasive manner through the vasculature and placed in the vein using a stent delivery system. Generally, to deliver and deploy one or more stents, one or more catheters may be advanced in a minimally invasive fashion through the vasculature to a target location. In some instances, a single catheter may be advanced to a target site in a blood vessel to deploy one or more stents. In other instances, a system comprising multiple catheters may be used to deliver and deploy one or more stents to different target sites in respective blood vessels. For example, in some instances a catheter may be placed in each of the two blood vessels (e.g., different veins). The catheter may comprise a push wire configured to advance within the catheter to push one or more stents out of a lumen of the catheter for deployment of a stent. For example, one or more stents may be pre-loaded into a lumen of the catheter distal to the push wire prior to introduction through vasculature. The push wire may be, for example, a guidewire, a stylet, a push rod, and the like. The push wire may be advanced within the catheter such that a distal end of the push wire pushes one or more stents out of the catheter and into a target blood vessel. The stent may be configured to self-deploy to a predetermined shape when advanced out of the catheter and into a target blood vessel by the push wire. In these instances, it should be appreciated that each catheter may or may not have the same configuration of elements, and that some catheters may be different from and/or complementary to other catheters. These devices and systems offer a minimally invasive approach that may improve procedural speed by permitting deployment of a plurality of struts using a single catheter and provide greater flexibility to allow stent delivery and deployment using smaller diameter blood vessels.

FIG. 6 illustrates a side view of a stent delivery system (600). As shown in FIG. 6, a stent delivery system (600) may comprise a catheter (610), a proximal adaptor (620) coupled to a proximal end of the catheter (610), a stent (630) configured to be compressed and advanced through the catheter (610), and a push wire (640) configured to push the stent (630) through and out of the catheter (610). The proximal adaptor (620) may help the stent transition from an expanded configuration to a compressed configuration to permit the stent to be advanced within a lumen of the catheter (610). Although shown in FIG. 6 as having a single port, the adaptor (620) may comprise any suitable number of ports (e.g., zero, one, two, three, or four or more), and the port may serve one or more useful functions (e.g., the introduction of one or more elements or substances into or through the catheter (610)). For example, the proximal adaptor (620) may be used to introduce one or more stents (630) into a lumen of the catheter (610). As another example, the proximal adaptor (620) may be used to introduce a fluid or substance (e.g., contrast agents, flush agents, therapeutic agents, and/or intravenous fluids) into a body lumen (not shown), and may be connected to a liquid or gaseous fluid source (e.g., a fluid pump, a syringe, etc.). The proximal adaptor (620) may further guide one or more devices (e.g., a push wire (640)) into a lumen of the catheter (610). Additional ports may be provided as desired for other functions, such as a visualization port, an actuator port, a suction port, and the like. Ports may have any suitable connection form factor, such as a threaded connector, luer connector, or the like.

In some variations, the one or more stents that may be loaded within a lumen of the catheter may have the stent dimensions described herein. In some instances, the stents may be configured to be compressible and biased to transition from a compressed configuration to an expanded configuration (e.g., self-expand). In some variations, the diaphanous nature of the stent allows radial compression to a diameter of about 0.035 inches or less, thereby allowing loading of the stent into a 4 Fr catheter or smaller. For example, the stent may be configured in a compressed configuration when loaded into a catheter and biased to self-expand to an expanded configuration when deployed from the catheter and into a target blood vessel having a larger diameter lumen than the catheter. The catheters may have any suitable diameter for intravascular use, such as, for example, about 4 French or less. Any suitable catheter or catheters may be used with the systems described herein to deploy the stents using the methods described herein. A push wire of the catheter may have a diameter of up to an inner diameter of the catheter. The push wire may have any suitable configuration (e.g., diameter) for pushing one or more loaded stents out of a distal end of the catheter. The stents may have the same or different dimensions and characteristics.

D. Fistula Formation System

Figure 4:
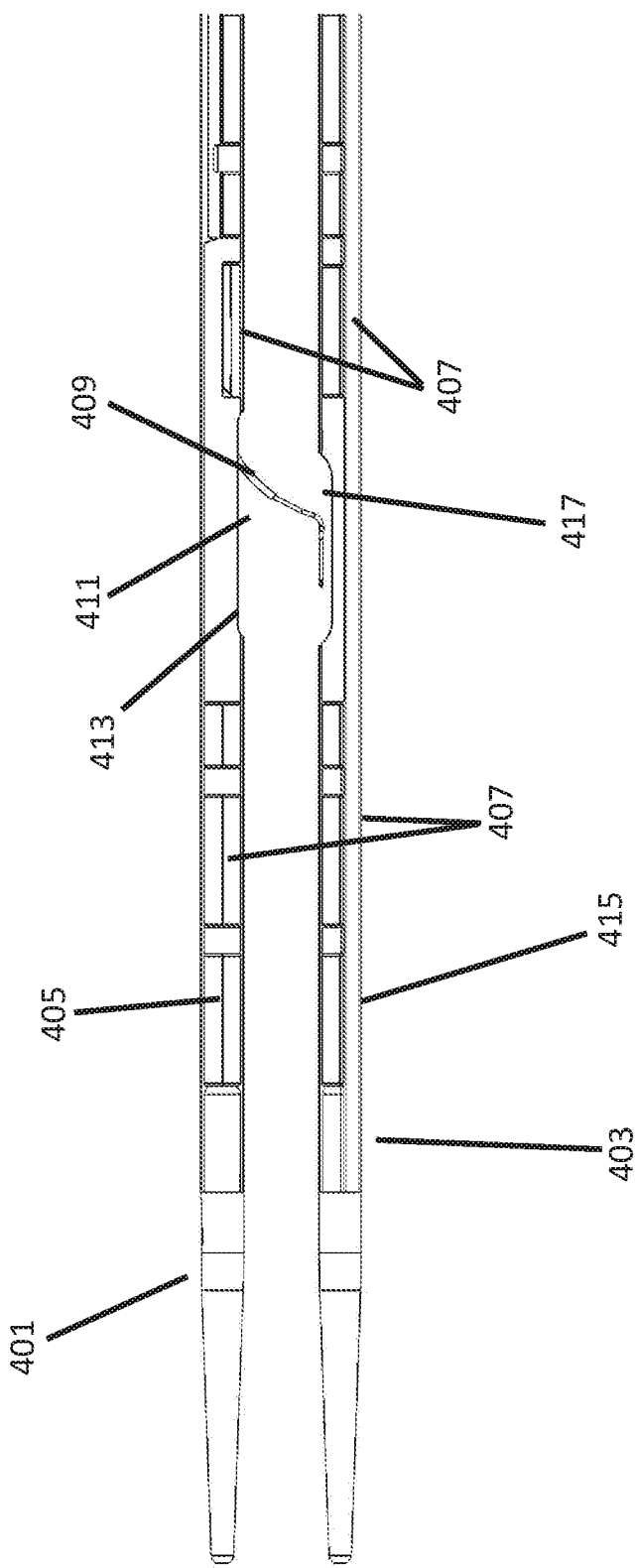
FIG. 4 depicts an illustrative variation of a system described here comprising a first catheter and a second catheter.

Also described here are systems for forming a fistula and improving retrograde blood flow through peripheral vasculature. Generally, the systems described here may comprise one or more catheters configured to be used to form a fistula in addition to a stent. FIG. 4 shows an illustrative variation of a catheter system that may be used to form a fistula as described herein. As shown there, the system may comprise a first catheter (401) and a second catheter (403). The first catheter (401) may comprise a catheter body (405), one or more magnetic elements (407), and a fistula-forming element (409) that may be used to form a fistula. In some variations, the fistula-forming element (409) may be advanced to project out of an opening (411) in the catheter body (405). The fistula-forming element (409) may comprise an electrode configured to move between a low-profile configuration and an extended configuration in which it extends from the catheter body (405). In some variations the fistula-forming element may be spring-biased toward the extended configuration. That is, the electrode may be configured to self-expand from the low-profile configuration to the extended configuration. Put yet another way, the electrode (409) may be in its natural resting state in the extended configuration. In some variations of electrodes moving between a low-profile configuration and an extended configuration, the electrode may be held in the low-profile configuration during placement of the catheter. For example, in some variations the electrode may be held in the low-profile configuration by the catheter body. The electrode may be released from the low-profile configuration when the electrode has been delivered to the location for fistula formation. For example, in some variations, the electrode may be released by moving the electrode in a proximal direction relative to the housing using a proximal control, as described in in U.S. patent application Ser. No. 13/298,169, filed on Nov. 16, 2011, and titled "DEVICES AND METHODS FOR FORMING A FISTULA," which is hereby incorporated by reference in its entirety. In other variations, the electrode may be held in a low-profile configuration by an external radially inward force on the electrode from a vessel wall during delivery, as described in U.S. patent application Ser. No. 15/406,755, filed on Jan. 15, 2017, and titled "DEVICES AND METHODS FOR FORMING A FISTULA" and claiming the benefit of U.S. Provisional Application Ser. No. 62/399,471, filed on Sep. 25, 2016, and U.S. Provisional Application Ser. No. 62/279,603, filed on Jan. 15, 2016, the contents of each of which are hereby incorporated by reference in its entirety.

In some variations, the first catheter (401) may comprise a housing (413), which may help protect other components of the first catheter (401) during fistula formation. For example, when the fistula-forming element (409) comprises an electrode configured to ablate tissue, the housing (413) may comprise one or more insulating materials which may shield or otherwise protect one or more components of the first catheter (401) from heat that may be generated by the electrode during use.

As shown in FIG. 4, the second catheter (403) may also comprise a catheter body (415) and one or more magnetic elements (407). In variations where the first catheter (401) comprises a fistula-forming element (409) configured to project out the catheter body (405) of the first catheter (401), such as the variation depicted in FIG. 4, the catheter body (415) of the second catheter (403) may comprise a recess (417) therein, which may be configured to receive the fistula-forming element (409) as it passes through tissue. While shown in FIG. 4 as having a recess (417), it should also be appreciated that in some variations the second catheter (403) may not comprise a recess (417). In some variations, the second catheter may comprise a fistula-forming element (not shown) in addition to or instead of the fistula-forming element (409) of the first catheter (401). Thus, in some variations, a fistula may be formed by one or more electrodes of one catheter, while in other variations, two catheters each comprising an electrode may simultaneously cut tissue from opposing sides to form a fistula.

Certain exemplary devices and systems that may be used in the methods described herein are described in more detail in U.S. patent application Ser. No. 13/298,169, filed on Nov. 16, 2011, and titled "DEVICES AND METHODS FOR FORMING A FISTULA," and U.S. patent application Ser. No. 15/406,755, filed on Jan. 15, 2017, and titled "DEVICES AND METHODS FOR FORMING A FISTULA," the contents of each of which was previously hereby incorporated by reference in its entirety.

II. Methods

Described here are methods for aiding cannulation, improving retrograde blood flow, and delivering a stent to a vessel using the systems and devices described herein. Generally, the stents described herein may be used to aid in cannulation by assisting in locating the blood vessel and/or by structurally supporting the blood vessel during cannulation. For example, the stents may reduce damage and/or prevent collapse of a blood vessel being punctured during cannulation. Additionally or alternatively, the stents described herein may be used to increase retrograde blood flow through a vein by being deployed into a vein segment to hold open one or more venous valves to permit retrograde blood flow. In some of these variations, a stent may be deployed in conjunction with formation of an arteriovenous fistula to provide arterialized blood flow in a vein and/or aid cannulation of the fistula.

Generally, the stents described herein may be deployed by self-expansion or balloon expansion. For instance, a self-expanding stent in a compressed configuration may be constrained by a stent delivery system (e.g., a system comprising a conduit configured to hold the self-expanding stent in a compressed configuration) as it is advanced through vasculature in a minimally-invasive manner. Upon delivery to a target vessel by the stent delivery system, the self-expanding stent may transition from the compressed configuration to an expanded configuration. The stent delivery system may be withdrawn from the target vessel and the stent may remain within the target vessel. Similarly, a balloon expandable stent in a compressed configuration may be coupled to a stent delivery system comprising a deflated balloon as it is advanced through vasculature in a minimally-invasive manner. At a deployment location, the balloon of the stent delivery system may be inflated to expandably deform the stent to an expanded configuration. After the balloon is deflated, and the stent delivery system withdrawn, the stent may remain in the expanded configuration within the target vessel.

In some variations, blood flow in a vessel may be improved using the catheters, stents, and corresponding methods described in U.S. patent application Ser. No. 15/406,755, filed on Jan. 15, 2017, and titled "DEVICES AND METHODS FOR FORMING A FISTULA" and claiming the benefit of U.S. Provisional Application Ser. No. 62/399,471, filed on Sep. 25, 2016, and U.S. Provisional Application Ser. No. 62/279,603, filed on Jan. 15, 2016, the contents of each of which was previously hereby incorporated by reference in its entirety.

A. Cannulation

Figure 5B:
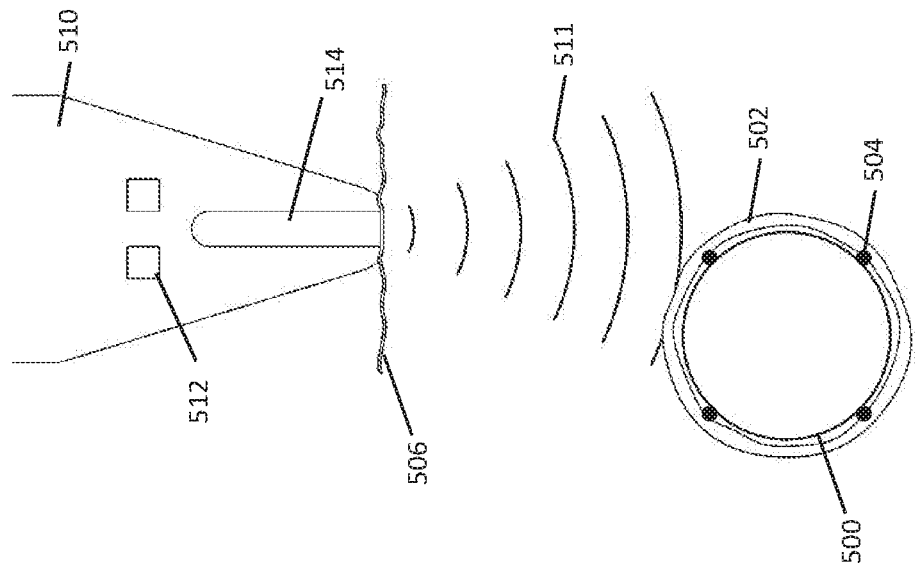
FIGS. 5A-5D depict an illustrative variation of a method for cannulating a vessel.
Figure 5A:
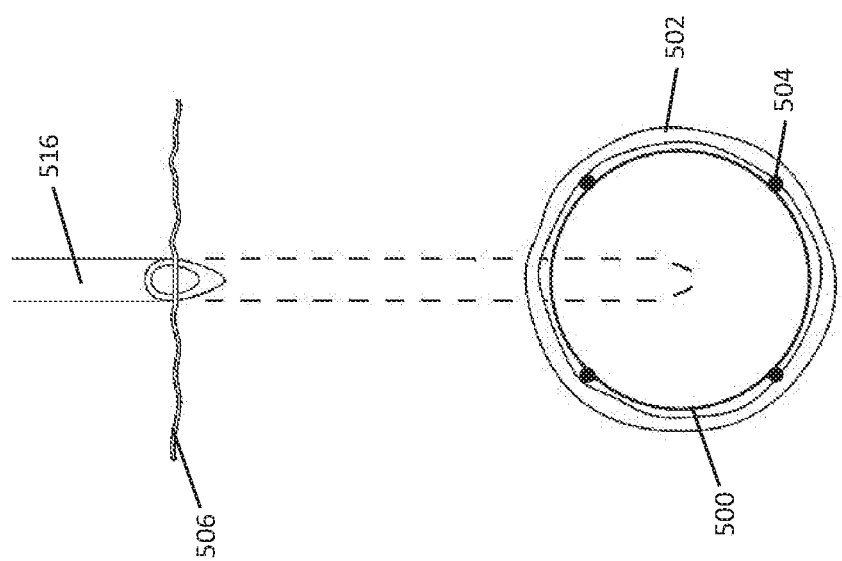
Figure 5D:
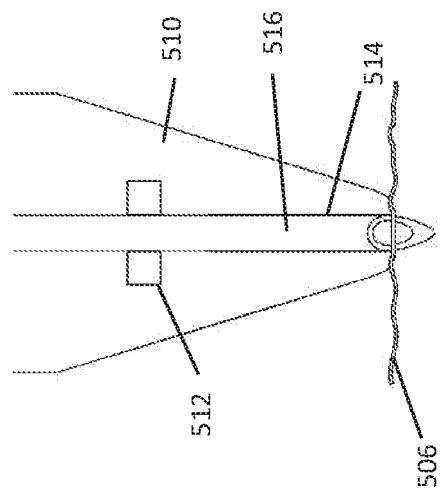

In some variations of the methods described here, the stents described herein may be used to aid in cannulation, such as by assisting in locating the blood vessel, and/or by structurally supporting the blood vessel during cannulation. FIG. 5A illustrates a cross-sectional view of a vessel and stent for cannulation. A stent (500) may be disposed in a blood vessel (502) beneath the skin (506). When the stent (500) is located in a vessel (502) having valves (504) (e.g., a peripheral vein), the stent (500) may be configured to hold open the valves (504). FIG. 5A depicts a needle (516) being inserted into the skin (506), blood vessel (502), and stent (500). In some variations, a stent (500) disposed in a vessel (502) may be more palpable than the vessel (502) alone, and thus may assist in location of the vessel (502). For example, when the skin (506) is palpated, the stent (500) may exhibit tympanic characteristics that may help an operator define a vessel and determine an access site.

A stent may additionally or alternatively assist in location of the vessel by allowing other forms of detection. For example, a stent detector may be used to locate the stent and therefore locate the blood vessel in which the stent is disposed. In some variations, a sensor of a stent detector may comprise a metal detector configured to detect a metal content of a stent disposed in a blood vessel. For example, the stent detector may be swept over a patient's skin. This may be useful where visualization and palpation of a vein is difficult due to a thick layer of adipose tissue. An example is shown in FIG. 5B where a stent detector (510) may be used to locate the stent (500), and therefore, the blood vessel (502) to be cannulated. The stent detector (510) may, for example, generate a magnetic field (511) used to detect a property of the stent (500) (e.g., metal). A display device (512) using one or more LEDs in FIG. 5B may indicate that a weak return signal of the stent (500) has been detected such that the stent detector (510) is near but not directly above the blood vessel (502). For example, a single LED emitting red light may indicate that the stent is within a peripheral sensor range of the stent detector. The color, intensity, pattern, etc. of the LED may change as the stent signal changes.

Figure 5C:
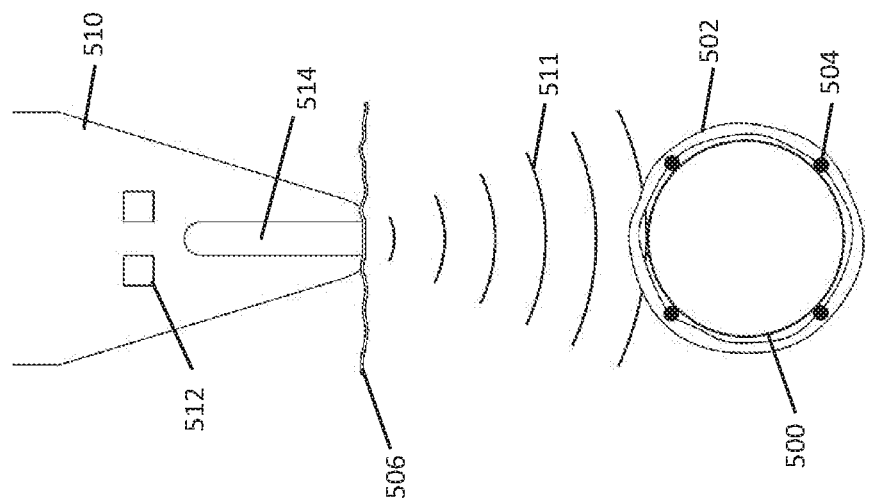

As shown in FIG. 5C, as an operator moves the stent detector (510) over the skin, the display (512) of the stent detector (510) may indicate that the stent detector (510) and cannulator (514) are located above the blood vessel (502) and stent (500) in a desired position for cannulation. For example, two LEDS may emit a green light that may indicate that the stent is below the stent detector within a predetermined sensor range. In this manner, the blood vessel (502) for cannulation may be located even through thick layers of adipose tissue. In some variations, a needle (516) may be loaded in a lumen of the cannulator (514) for advancement through the skin (506), blood vessel (502), and stent (500). These devices and systems offer a non-invasive approach to determining a blood vessel location, having improved procedural speed.

A stent may additionally or alternatively assist in cannulation by structurally supporting the blood vessel during cannulation. For example, in some cases, cannulation of an arterialized vein may collapse the vein due to insufficient blood pressure. However, a stent disposed in a vein segment may increase the strength and stiffness of a portion of the vein to withstand cannulation without vein collapse and/or back-walling of the needle. Furthermore, cannulation of a vein may in some cases cause infiltration of the vein where blood leaks out of the vein and causes swelling in the perivascular space (e.g., hematoma). Infiltration may compress the vessel and cause an undesirable thrombosis. A stent disposed in the blood vessel may increase the radial strength of the vessel to reduce the compressive forces of cannulation and infiltration from closing the blood vessel shut.

B. Retrograde Flow

The methods described herein may also increase retrograde blood flow through a vein. Generally, the methods may comprise advancing one or more stents into peripheral vasculature. The stent may be deployed into a vein segment to hold open one or more valves. The stent may provide force on the venous valves to hold the leaflets of the valves in an open configuration. As such, the stent may hold one or more venous valves to frustrate the valves without cutting them. Furthermore, deployment of the stent may be faster and simpler than use of a valvulotome. For instance, deployment of the stent in a vessel may be performed without visualization (e.g., contrast injection) due to the symmetric and repeating configuration of the stent. Moreover, the sidewalls of the stent may additively increase the radial strength of the vein vessel walls, as described in more detail herein.

As mentioned above, use of a stent in venous tissue to frustrate one or more venous valves may be performed in fewer steps than a valvulotomy. A valvulotomy procedure to increase retrograde blood flow through a vein may require a user to visualize and locate a valve (e.g., using contrast), unsheathe the valvulotome, cut the leaflets with the valvulotome, resheath the valvulotome, and repeat the process for each valve to be cut. This may be a time consuming process, as the location, size, and spacing of valves in peripheral vasculature varies per individual. By contrast, a venous stent having a length sufficient to cover a desired vein segment may be located and deployed once to hold a plurality of valves in an open configuration irrespective of the location, size, and spacing of the valves. Put another way, a venous stent may in some instances prevent valve function over a desired vein segment in fewer steps and less time than a valvulotome. In addition, use of a venous stent to frustrate valves may be reversible (i.e., the stent may be removed from the vein to regain valve function), in contrast to a valvulotomy.

A length of a stent may be varied based on a desired length of retrograde blood flow in the vessel. For example, a longer stent disposed in a vein segment will cover and render incompetent a greater number of venous valves and thus allow for distal blood flow along a greater length of the vein. It may be desirable for the distal portion of the stent to have a minimal thickness and surface area necessary to hold open the venous valves.

In some variations, a stent may also increase retrograde blood flow through a vein by forming a proximal thrombus. For example, a stent may be configured to form a thrombus after being delivered to a vessel. Blood flow through the fistula may be thus be diverted distally to flow retrograde through the vein at a predetermined rate (e.g., over a week). A proximal portion of a stent may comprise, for example, copper to induce a thrombus over time. In other variations, the proximal portion of the stent may be electroplated, comprise a coating for inducing thrombosis, and/or be made of a thrombogenic fiber. Alternatively, the proximal portion of the stent may comprise a semi-permeable or impermeable membrane (e.g., cap, plug) to immediately reduce and/or eliminate proximal venous blood flow back to the heart. A distal portion of the stent may be configured to permit unobstructed blood flow through a lumen of the vein (e.g., by frustrating the venous valves). The distal portion may in some variations be configured to prevent platelet aggregation and maximize retrograde blood flow through the vein.

C. In Conjunction with a Fistula

The systems and methods described here may be used in some variations for cannulation of a fistula, such as for dialysis access. In some variations, the methods may comprise deploying a stent in conjunction with formation of an arteriovenous fistula to ease cannulation of the fistula, and/or to allow for additional cannulation sites. The fistula may in some variations be a surgically formed fistula. In other variations, the fistula may be formed by a minimally invasive procedure. For example, the fistula may be formed endovascularly using a catheter system as described herein.

More particularly, in some variations a fistula may be formed using a minimally invasive procedure by accessing a first blood vessel with a first catheter, and advancing the first catheter to a target location within a first blood vessel. A second blood vessel may be accessed with a second catheter, and the second catheter may be advanced to a target location within the second vessel. After the vessels are brought toward each other and aligned, one or more fistula-forming elements may be activated to bore through, perforate, or otherwise create a passageway between the two blood vessels such that blood may flow directly between the two adjoining blood vessels.

In some variations of methods in which a fistula is formed using a catheter system, the methods described herein may comprise aligning the first and second catheters. This may axially and/or rotationally align the catheters. For example, the catheters may be oriented such that a fistula-forming element of at least one of the first or second catheter is positioned to form a fistula in a certain location. In variations where both the first and second catheters comprise fistula-forming elements (e.g., an active electrode and a ground electrode, or each an active electrode), the catheters may be oriented to align these fistula-forming elements. The catheters may be aligned in any suitable manner. The first and second catheters may comprise any alignment element or combination of alignment elements. In some variations, each of the first and second catheters may comprise one or more magnetic alignment elements, which may generate an attractive force between the first and second catheters. This may pull the catheters toward each other and/or help to rotationally align them. Once the catheter or catheters are in position, one or more fistula-forming elements may be used to create a fistula between the two blood vessels, as described in more detail in U.S. patent application Ser. No. 13/298,169, filed on Nov. 16, 2011, and titled "DEVICES AND METHODS FOR FORMING A FISTULA," and U.S. patent application Ser. No. 15/406,755, filed on Jan. 15, 2017, and titled "DEVICES AND METHODS FOR FORMING A FISTULA," each of which was previously incorporated by reference in its entirety.

The methods involving stents described herein may allow for easier cannulation of a fistula, for example to allow for dialysis access, by assisting with locating the access site and/or by structurally supporting the blood vessel during cannulation, as described in more detail herein. Furthermore, the methods involving stents described herein may allow for additional cannulation sites by allowing for retrograde flow. For example, a venous stent may allow for cannulation in the forearm region of a patient. This may be desirable because a vessel for vascular access in hemodialysis is ideally located about 5 mm or less from the skin of the patient. However, some vessels, particularly in the upper arm, may be too deep below the skin for palpation and/or visualization due to an underlying layer of adipose tissue.

In some variations, the methods described herein may comprise forming a fistula and deploying a stent in vein, such as a cephalic vein and/or basilic vein. Arterialized blood flow may flow distally from the fistula and through the stent until meeting one or more accessory branches, at which point a portion of the retrograde blood may flow proximally through the one more accessory branches proximally towards the heart. Thus, the stent may define or expand a cannulation region (e.g., vein segment) having arterialized retrograde blood flow. In one particular variation, a stent as described herein may be deployed in the cephalic vein to frustrate the venous valves and allow for retrograde flow from a fistula distally. The stent may be placed distal to or through the region of the elbow crease and the forearm until the cephalic vein meets the accessory cephalic vein. This may allow cannulation of the cephalic vein in the forearm region. In this example, blood flow may return proximally via the accessory cephalic vein. The stent may additionally assist with cannulation in the forearm region by assisting with locating the vessel and structurally supporting the vein, as described herein.

Additionally or alternatively, a portion of a stent located in a vein proximally to a fistula may be used to form a thrombosis to drive arterial blood flow distally through the vein. In some of these variations, a portion of the stent may cover the fistula, and blood flow through the fistula may travel through the sidewall of the stent. The stent may form a thrombus as described in more detail herein. For example, a proximal portion of the stent may comprise copper to induce thrombus over time (e.g., a week). In other variations, the proximal portion of the stent may be electroplated, comprise a coating for inducing thrombosis, and/or be made of a thrombogenic fiber. Alternatively, the proximal portion of the stent may comprise a semi-permeable or impermeable membrane (e.g., cap, plug) to immediately reduce and/or eliminate proximal venous blood flow back to the heart. An intermediate portion of the stent, disposed between a proximal portion and a distal portion, may be disposed over a fistula and may be porous to permit blood flow from the fistula to flow into the vein. A distal portion of the stent may be configured to permit unobstructed blood flow through a lumen of the vein (e.g., by frustrating the venous valves).

D. Stent Delivery

The methods described herein may also deliver one or more of the stents described herein into a target vessel. Generally, the methods may comprise advancing and deploying one or more stents into peripheral vasculature using a single catheter. The use of the devices and systems described herein may be performed in fewer steps than using conventional stent delivery systems. Typical stent delivery systems include a catheter provided individually per stent. For example, a single stent is typically affixed to an end of a catheter and covered by an outer sleeve during advancement through vasculature. Once the stent is advanced to a desired location, the outer sleeve may be retracted so as to allow the stent to expand (e.g., using self-expansion and/or balloon expansion) and deploy into a target blood vessel. These systems using a catheter and sleeve are typically 6 French and greater in diameter. Accordingly, deployment of a plurality of stents may be a time consuming process that requires a set of corresponding delivery systems. By contrast, the stent delivery methods and systems described herein provide an easily operated and adaptable catheter that may be configured to deploy a plurality of stents sequentially without advancing and withdrawing individual catheters. Put another way, one or more stents may in some instances be deployed into one or more target blood vessel segments in fewer steps and less time than conventional stent delivery systems. The stents may have different configurations and be loaded sequentially together in the catheter. The stents may be configured with different dimensions, characteristics, and functions. For example, stents configured for vessel support may differ in one or more of materials, compressibility, detection, diameter, strut thickness, etc., from stents configured for vessel visualization. In addition, the stent delivery catheters described herein may have a compact configuration that allows advancement and deployment of stents in small diameter vessels.

Figure 7A:
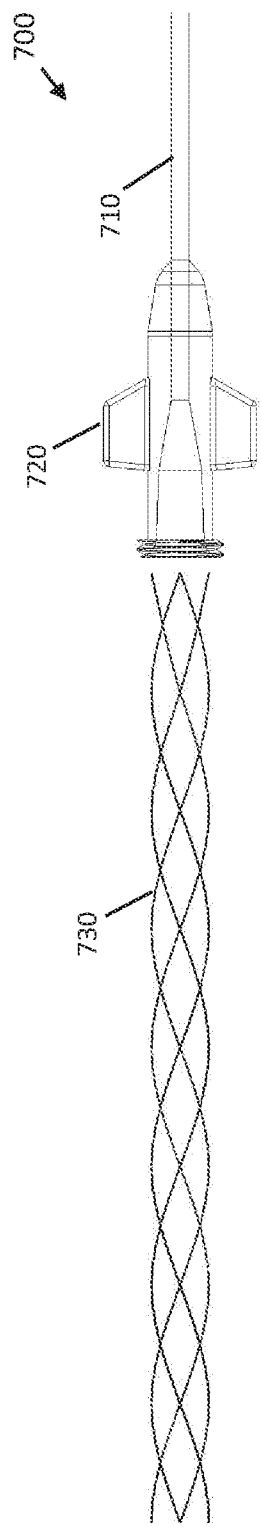
FIGS. 7A-7E depict illustrative variations of a method for delivering a stent.
Figure 7B:
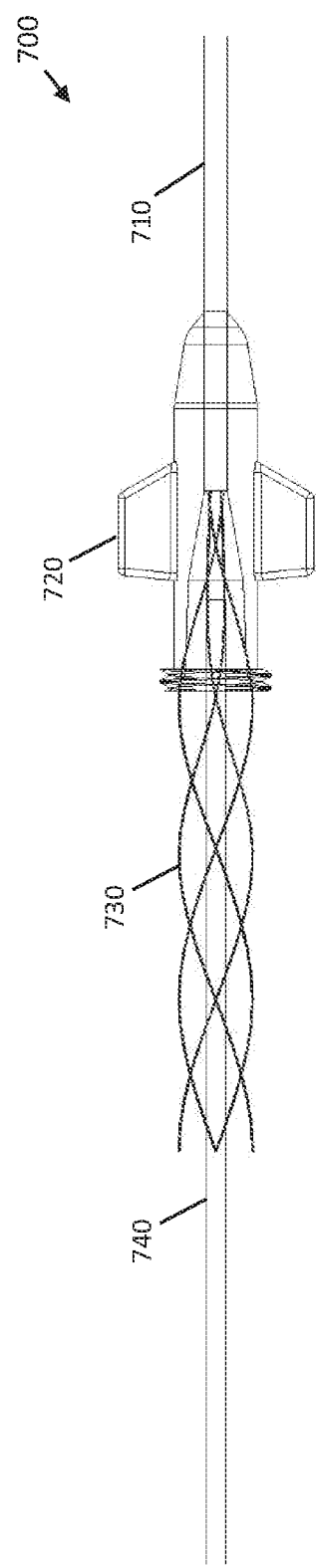
Figure 7C:
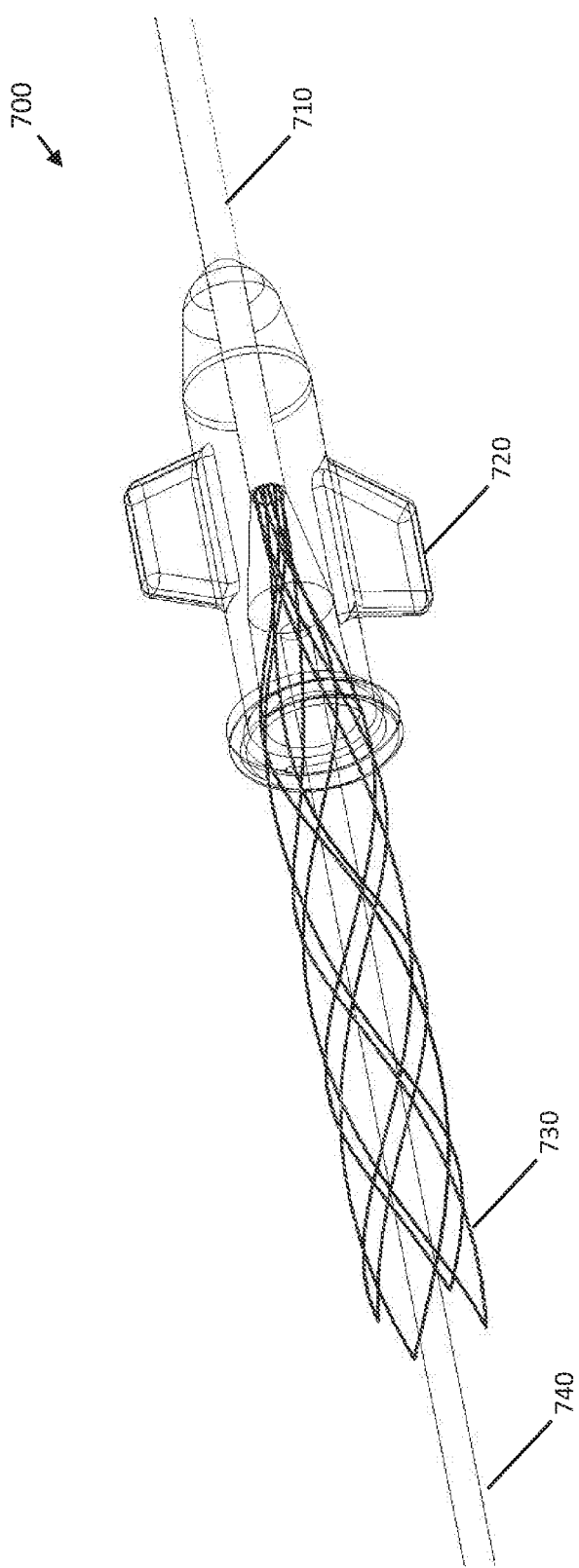

In some variations, one or more stents may be deployed using a minimally invasive procedure by accessing a blood vessel with a catheter, and advancing the catheter to a target location within the blood vessel. FIGS. 7A-7E show illustrative steps of a method for delivering a stent (730). FIG. 7A illustrates a cross-sectional side view of a proximal end of a stent delivery system (700) with a stent (730) in position to be inserted into a lumen of the catheter (710). The stent (730) may be introduced into a proximal end of a catheter (710) through a proximal adaptor (720). The system (700) may include a catheter (710) coupled to the proximal adaptor (720). In some variations, the stent (730) may be biased to be in an expanded configuration (as shown in FIG. 7A). FIGS. 7B and 7C are respective cross-sectional side and perspective views of the stent (730) and a push wire (740) being introduced into a proximal opening of the proximal adaptor (720). An inner diameter of the adaptor (720) may taper to match the catheter (710) coupled to the adaptor (720). As the stent (730) in an expanded configuration is introduced further into the adaptor (720), the inner diameter of the adaptor (720) decreases and the diaphanous stent (730) may begin to transition from the expanded configuration into a compressed configuration, thereby allowing the stent (730) to be introduced into a proximal end of the catheter (710) and slidably advanced in the compressed configuration. As the push wire (740) is introduced into the catheter (710), the adaptor (720) may guide the push wire (740) into a lumen of the catheter (710). For ease of illustration in FIGS. 7B and 7C, stent (730) and push wire (740) are shown as being introduced together into the adaptor (720). However, one or more stents (730) may be introduced sequentially into the catheter (710) prior to the push wire (740) such that a proximal end of one of the stents (730) may abut a distal end of the push wire (740).

Figure 7D:
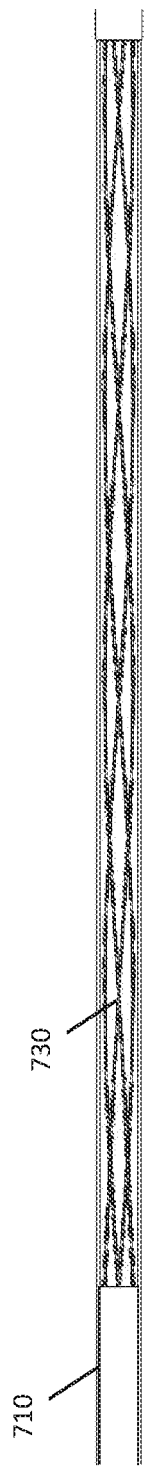

FIG. 7D illustrates a cross-sectional side view of a stent (730) in a compressed configuration within a lumen of the catheter (710). The stents may have the same or different configuration, so long as they may be disposed within a lumen of the catheter (710) in a compressed configuration. In some variations, the catheter (710) may be loaded with one or more stents (730) outside of the body. The push wire (740) may be advanced into the catheter (710) and disposed proximal to the loaded stents (730). In other variations, the catheter (710) may be introduced and advanced into vasculature in a minimally invasive manner prior to loading the catheter (710) with one or more stents (730) and push wire (740). Additionally or alternatively, a first set of stents may be introduced into the catheter (710) prior to a minimally invasive procedure. After the deployment of the first set of stents in one or more target vessels, the catheter (710) may be repositioned at a desired location, the push wire (740) may be retracted from a proximal end of the catheter (710), and a second set of stents may be introduced and loaded into the catheter (710).

Figure 7E:
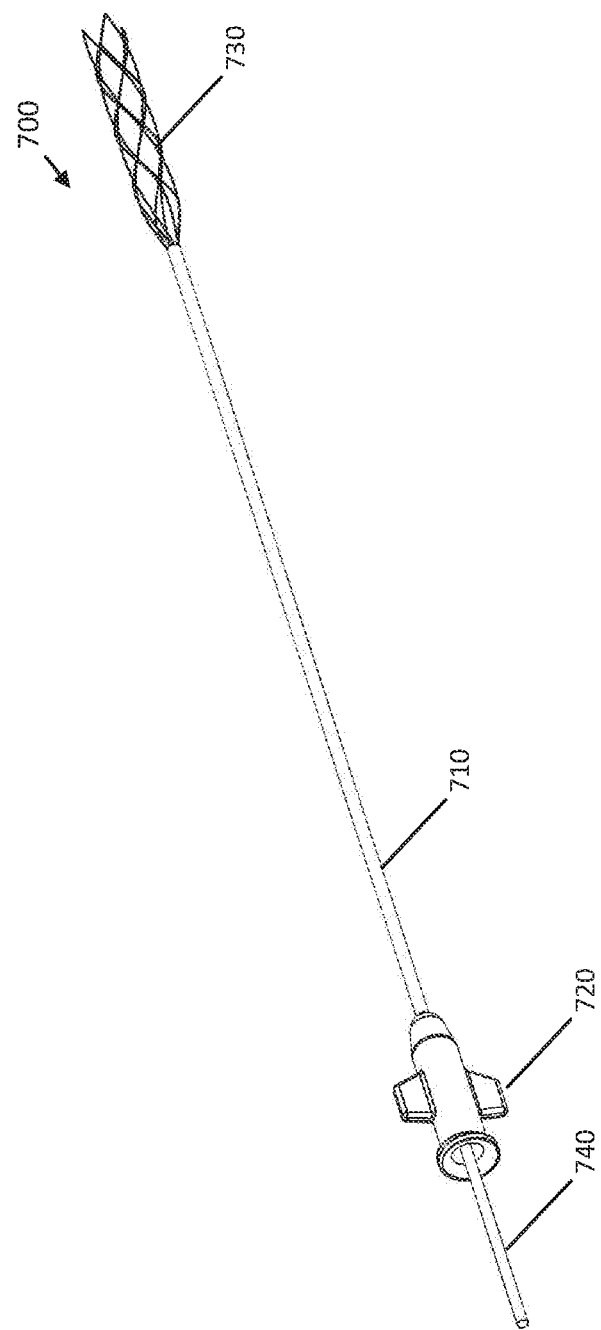

Once a distal end of the catheter (710) is positioned at a predetermined deployment location, the push wire (740) may be advanced within the catheter (710) to push the one or more stents (730) out of the distal end of the catheter (710) and into the target blood vessel. FIG. 7E is a perspective view of the catheter system (700) deploying a stent from a distal end of the catheter (710). Although not shown in FIG. 7E, a distal end (e.g., distal tip) of the push wire (740) may contact and push a proximal end of the stent (730) while the catheter (710) is stationary relative to the target blood vessel so as to advance the stent (730) out of the catheter (710) and deploy the stent (730) in the target blood vessel. Alternatively, the stent (730) may be advanced and deployed out of the catheter (710) by retracting the catheter (710) while the push wire (740) is stationary relative to the target blood vessel.

In some variations, the stent (730) disposed in the catheter (710) is in a compressed configuration and transitions to an expanded configuration upon advancement out of the catheter (710) and into the target blood vessel. For example, the stent (730) may self-expand as the stent (730) is advanced into the target blood vessel having a larger diameter lumen than that of the catheter (710). In other variations, a balloon may be used to transition the stent into an expanded configuration through balloon inflation.

In variations in which a plurality of stents (730) are to be deployed, the stents (730) may be deployed in a sequential manner by advancement of the push wire (740) and/or retraction of the catheter (710). As one non-limiting example, a first stent may be deployed in a first blood vessel (e.g., vein) portion by advancing the push wire (740) to push the first stent out of the catheter (710) while the catheter (710) remains fixed relative to the first blood vessel. The first stent may self-expand (e.g., bias to form the expanded configuration) once disposed in the first blood vessel. The catheter (710) may be advanced through vasculature to another predetermined location and then used to deploy a second stent in a second vein portion by further advancing the push wire (740) to push the second stent out of the catheter (710). A third stent may be deployed in the second vein portion by retracting the catheter (710) relative to the second vein portion while maintaining the push wire (740) in position. The second and third stents may self-expand once disposed in the target blood vessel.

Although the foregoing variations have, for the purposes of clarity and understanding, been described in some detail by of illustration and example, it will be apparent that certain changes and modifications may be practiced, and are intended to fall within the scope of the appended claims. Additionally, it should be understood that the components and characteristics of the devices described herein may be used in any combination. The description of certain elements or characteristics with respect to a specific figure are not intended to be limiting or nor should they be interpreted to suggest that the element cannot be used in combination with any of the other described elements.

We claim:

1. A method for cannulating a first vessel comprising:
   advancing a stent into the first vessel comprising one or more valves;
   deploying the stent over the one or more valves to hold open the one or more valves;
   non-invasively detecting a stent location of the stent with a stent detector; and
   advancing a needle through a wall of the first vessel, wherein the stent detector is coupled to a needle injector of the needle.

2. The method of claim 1, wherein the needle is advanced through an aperture defined in a wall of the stent.

3. The method of claim 1, wherein the needle is advanced through the wall of the first vessel distal to the stent.

4. The method of claim 1, further comprising positioning the needle over the first vessel using the detected stent location.

5. The method of claim 1, wherein the stent comprises first struts and second struts having different thicknesses.

6. The method of claim 1, wherein the first vessel is a cephalic vein.

7. The method of claim 1, wherein the first vessel is a basilic vein.

8. The method of claim 1, further comprising advancing a first catheter into an artery adjacent to a vein, wherein the first catheter comprises a fistula-forming element, and forming a fistula between the artery and the vein using the fistula-forming element.

9. The method of claim 8, wherein the stent is deployed distal to the fistula.

10. The method of claim 8, wherein the artery is an ulnar artery and the vein is an ulnar vein.

11. The method of claim 8, further comprising advancing a second catheter into the vein.

12. The method of claim 11, further comprising aligning the first catheter and the second catheter.

13. The method of claim 1, further comprising loading one or more stents into a third catheter, and deploying the one or more stents sequentially from the third catheter into the first vessel by advancing a push wire through the third catheter.

* * * * *